US008057756B2

(12) United States Patent
Londo et al.

(10) Patent No.: US 8,057,756 B2
(45) Date of Patent: Nov. 15, 2011

(54) SAMPLING PROBE, GRIPPER AND INTERFACE FOR LABORATORY SAMPLE MANAGEMENT SYSTEMS

(75) Inventors: Thomas R. Londo, Ashland, MA (US); Paul M. Grippo, Bedford, NH (US); Frank Sylva, Billerica, MA (US); Charles Schelberg, Milford, NH (US); Jeff Finkelstein, Charlotte, VT (US); Mark Lyons, Charlotte, VT (US)

(73) Assignee: Parker-Hannifin Corporation, Cleveland, OH (US)

( * ) Notice: Subject to any disclaimer, the term of this patent is extended or adjusted under 35 U.S.C. 154(b) by 346 days.

(21) Appl. No.: 11/814,987

(22) PCT Filed: Jan. 27, 2006

(86) PCT No.: PCT/US2006/002845
§ 371 (c)(1),
(2), (4) Date: Jul. 27, 2007

(87) PCT Pub. No.: WO2006/083695
PCT Pub. Date: Aug. 10, 2006

(65) Prior Publication Data
US 2008/0156117 A1 Jul. 3, 2008

Related U.S. Application Data

(60) Provisional application No. 60/648,213, filed on Jan. 28, 2005.

(51) Int. Cl.
*B01L 3/02* (2006.01)
(52) U.S. Cl. .... 422/501; 73/863.32; 73/864; 73/864.01; 73/864.11; 422/500; 422/502

(58) Field of Classification Search .................... 73/864, 73/864.01, 864.11, 64.13, 864.13, 864.14, 73/864.16, 864.24, 864.87, 863.22; 206/571; 422/99, 100, 500, 501, 502, 511, 517
See application file for complete search history.

(56) References Cited

U.S. PATENT DOCUMENTS

| 2,771,217 A * | 11/1956 | Brown et al. .................. 222/43 |
| 3,279,659 A | 10/1966 | Harris, Jr. |
| 3,401,692 A | 9/1968 | Harris, Jr. |

(Continued)

FOREIGN PATENT DOCUMENTS

CA    2 047 636    7/1991

(Continued)

OTHER PUBLICATIONS

Agilent Technologies, Agilent 1100 Series Injection Systems, Mar. 1, 2004, 8 pages.

(Continued)

*Primary Examiner* — David A. Rogers
(74) *Attorney, Agent, or Firm* — Renner, Otto, Boisselle & Sklar, LLP

(57) ABSTRACT

A self-contained sampling probe characterized by a drive module and a syringe module removably coupled coaxially to the drive module to allow for different syringe modules to be interchangeably coupled to the drive module. The coupling is effected by quick connect and disconnect devices, and the syringe module may carry an identifier. The probe is engageable by a gripper or insertable in an interface device, both of which provide for communication of the probe with other system components.

10 Claims, 15 Drawing Sheets

U.S. PATENT DOCUMENTS

| | | | |
|---|---|---|---|
| 3,489,525 A | 1/1970 | Natelon | |
| 3,498,135 A * | 3/1970 | Jerg et al. | 73/864.18 |
| 3,604,267 A * | 9/1971 | Johns | 73/864.82 |
| 3,738,493 A | 6/1973 | Cummins et al. | |
| 3,866,476 A | 2/1975 | Thomas | |
| 3,912,456 A | 10/1975 | Young | |
| 3,915,651 A | 10/1975 | Nishi | |
| 3,954,617 A | 5/1976 | Ishimatsu | |
| 3,957,051 A | 5/1976 | Topham | |
| 3,991,616 A | 11/1976 | Stahli | |
| 4,094,197 A | 6/1978 | Harris, Sr. et al. | |
| 4,098,125 A * | 7/1978 | Lee | 73/864.13 |
| 4,106,911 A | 8/1978 | Marcelli | |
| 4,162,030 A | 7/1979 | Capra et al. | |
| 4,182,184 A | 1/1980 | Bakalyar et al. | |
| 4,204,430 A | 5/1980 | Huber et al. | |
| 4,217,780 A | 8/1980 | O'Connell et al. | |
| 4,276,048 A | 6/1981 | Leaback | |
| 4,283,950 A * | 8/1981 | Tervamaki | 73/864.14 |
| 4,310,057 A | 1/1982 | Brame | |
| 4,346,742 A | 8/1982 | Chase | |
| 4,362,064 A * | 12/1982 | Marteau d'Autry | 73/864.13 |
| 4,399,711 A * | 8/1983 | Klein | 73/864.16 |
| 4,459,864 A | 7/1984 | Cirincione | |
| 4,487,081 A * | 12/1984 | De Vaughn et al. | 73/864.13 |
| 4,519,258 A | 5/1985 | Jakubowicz | |
| 4,563,907 A | 1/1986 | Johnson, Jr. et al. | |
| 4,621,534 A | 11/1986 | Munari et al. | |
| 4,624,148 A | 11/1986 | Averette | |
| 4,676,951 A | 6/1987 | Armes et al. | |
| 4,681,741 A | 7/1987 | Hanaway | |
| 4,713,974 A | 12/1987 | Stone | |
| 4,769,009 A | 9/1988 | Dykstra | |
| 4,821,586 A | 4/1989 | Scordato et al. | |
| 4,833,384 A | 5/1989 | Munro et al. | |
| 4,984,475 A | 1/1991 | Uffenheimer et al. | |
| 4,989,623 A | 2/1991 | Hoffman et al. | |
| 5,055,263 A | 10/1991 | Meltzer | |
| 5,133,218 A | 7/1992 | Uffenhiemer et al. | |
| 5,158,748 A | 10/1992 | Obi et al. | |
| 5,176,646 A | 1/1993 | Kuroda | |
| 5,183,638 A | 2/1993 | Wakatake | |
| 5,186,194 A | 2/1993 | Kitajima | |
| 5,187,990 A | 2/1993 | Magnussen, Jr. et al. | |
| 5,238,654 A | 8/1993 | Nohl et al. | |
| 5,277,871 A | 1/1994 | Fujii et al. | |
| 5,328,654 A | 7/1994 | Dixit | |
| 5,348,585 A | 9/1994 | Weston | |
| 5,401,253 A | 3/1995 | Reynolds | |
| D360,462 S * | 7/1995 | Armbruster et al. | D24/113 |
| 5,567,122 A | 10/1996 | Schulte | |
| 5,650,122 A | 7/1997 | Harris et al. | |
| 5,651,775 A | 7/1997 | Walker et al. | |
| 5,660,792 A | 8/1997 | Koike | |
| 5,734,424 A | 3/1998 | Sasaki | |
| 5,743,886 A | 4/1998 | Lynn et al. | |
| 5,776,414 A | 7/1998 | Itani et al. | |
| 5,795,333 A * | 8/1998 | Reilly et al. | 604/154 |
| 5,897,837 A | 4/1999 | Mizuno | |
| 5,983,733 A * | 11/1999 | Strandberg et al. | 73/864.11 |
| 6,019,004 A * | 2/2000 | Conley et al. | 73/864.16 |
| 6,033,911 A | 3/2000 | Schultz et al. | |
| 6,060,022 A | 5/2000 | Pang et al. | |
| 6,143,252 A | 11/2000 | Haxo, Jr. et al. | |
| 6,143,573 A | 11/2000 | Rao et al. | |
| 6,146,594 A | 11/2000 | De Graaff et al. | |
| 6,241,950 B1 | 6/2001 | Veelenturf et al. | |
| 6,299,841 B1 * | 10/2001 | Rainin et al. | 422/100 |
| 6,343,717 B1 | 2/2002 | Zhang et al. | |
| 6,360,794 B1 | 3/2002 | Turner | |
| 6,374,683 B1 | 4/2002 | Hunicke-Smith et al. | |
| 6,387,330 B1 | 5/2002 | Bova et al. | |
| 6,401,769 B1 | 6/2002 | Backes et al. | |
| 6,406,632 B1 | 6/2002 | Safir et al. | |
| 6,422,248 B1 | 7/2002 | Fuerst et al. | |
| 6,526,812 B2 | 3/2003 | Martin et al. | |
| 6,551,557 B1 | 4/2003 | Rose et al. | |
| 6,569,127 B1 * | 5/2003 | Fago et al. | 604/218 |
| 6,585,700 B1 * | 7/2003 | Trocki et al. | 604/218 |
| 6,662,626 B2 | 12/2003 | van der Maas | |
| 6,694,197 B1 | 2/2004 | Hatcher et al. | |
| 6,740,295 B2 | 5/2004 | Braun et al. | |
| 6,814,936 B1 * | 11/2004 | Enhorning | 422/100 |
| 6,819,420 B2 | 11/2004 | Kuebler et al. | |
| 6,846,680 B2 | 1/2005 | Friswell et al. | |
| 6,884,231 B1 | 4/2005 | Walters et al. | |
| 6,902,703 B2 | 6/2005 | Marouiss et al. | |
| 6,932,939 B2 | 8/2005 | Ozbal et al. | |
| 6,945,128 B2 | 9/2005 | Ford et al. | |
| 6,968,749 B2 * | 11/2005 | Chen et al. | 73/863.32 |
| 6,983,636 B2 | 1/2006 | Johnson et al. | |
| 7,071,000 B2 | 7/2006 | Wang et al. | |
| 7,125,727 B2 | 10/2006 | Massaro | |
| 7,146,867 B2 * | 12/2006 | Jagdhuber | 73/863.32 |
| 7,160,511 B2 | 1/2007 | Takahashi et al. | |
| 7,214,540 B2 | 5/2007 | DeLucas et al. | |
| 7,234,365 B2 | 6/2007 | Carlson et al. | |
| 7,244,396 B2 | 7/2007 | Chait et al. | |
| 7,284,454 B2 | 10/2007 | Cote | |
| 7,314,598 B2 * | 1/2008 | Nishino | 422/100 |
| 7,377,189 B2 * | 5/2008 | Champseix et al. | 73/864.25 |
| 2001/0011630 A1 | 8/2001 | Loschner et al. | |
| 2001/0019845 A1 | 9/2001 | Bienert et al. | |
| 2002/0076351 A1 | 6/2002 | Wernz et al. | |
| 2002/0190202 A1 | 12/2002 | Liang | |
| 2002/0192113 A1 | 12/2002 | Uffenheimer et al. | |
| 2004/0022680 A1 | 2/2004 | Gueller et al. | |
| 2004/0022688 A1 * | 2/2004 | Blackwood | 422/100 |
| 2004/0024364 A1 | 2/2004 | Langley et al. | |
| 2004/0096360 A1 | 5/2004 | Toi et al. | |
| 2004/0123650 A1 | 7/2004 | Kolosov et al. | |
| 2004/0123681 A1 | 7/2004 | Thomas et al. | |
| 2004/0133183 A1 * | 7/2004 | Trocki et al. | 604/500 |
| 2004/0211247 A1 | 10/2004 | Hajduk et al. | |
| 2004/0219071 A1 | 11/2004 | Ozbal et al. | |
| 2005/0123970 A1 | 6/2005 | Ozbal et al. | |
| 2005/0155438 A1 | 7/2005 | Belgardt | |
| 2005/0215983 A1 * | 9/2005 | Brock | 606/1 |
| 2005/0220676 A1 * | 10/2005 | Tran | 422/100 |
| 2006/0069354 A1 * | 3/2006 | Buenger et al. | 604/198 |
| 2006/0099115 A1 * | 5/2006 | Sandberg | 422/100 |
| 2006/0144942 A1 | 7/2006 | Evans et al. | |
| 2006/0213257 A1 | 9/2006 | Togashi et al. | |
| 2007/0062583 A1 | 3/2007 | Cox et al. | |

FOREIGN PATENT DOCUMENTS

| | | |
|---|---|---|
| DE | 2926691 | 6/1981 |
| DE | 3805808 | 9/1989 |
| DE | 4318919 | 12/1994 |
| DE | 4341229 | 6/1995 |
| DE | 102 57 414 | 6/2004 |
| EP | 0141148 | 5/1985 |
| EP | 0235120 | 9/1987 |
| EP | 428500 A2 * | 5/1991 |
| EP | 0 469 444 | 6/1997 |
| EP | 0 801 309 | 10/1997 |
| EP | 1275957 | 1/2003 |
| EP | 1 559 480 | 8/2005 |
| GB | 1484539 | 9/1977 |
| JP | 200128160 | 9/2001 |
| WO | 91/07662 | 5/1991 |
| WO | 97/03766 | 2/1997 |
| WO | 02/085521 | 10/2002 |
| WO | 2004/099059 | 11/2004 |
| WO | 2004/102182 | 11/2004 |
| WO | 2005/039771 | 5/2005 |
| WO | 2006/128662 | 12/2006 |
| WO | 2007041843 | 4/2007 |

OTHER PUBLICATIONS

CTC Analytics AG, Front End Automation Systems for Liquid Chromatography, 6 pages.

Perkin Elmer Instruments, Series 200 Autosampler New Standard in automated sample processing, 2001, 8 pages.

Ring-Ling Chien et al., Parallel High Performance Liquid Chromatography, 1 page.
Shimadzu Corporation, Prominence Shimadzu High Performance Liquid Chromatograph, 3 pages.
Shimadzu Corporation, High throughput LC injection system, 2 pages.
Shimadzu Corporation, Autosampler for Shimadzu VP series HPLC System, 2 pages.
Thermo Electron Corporation, TriPlus Autosampler Flexible Sampling Solutions, 2004, 2 pages.
Waters, Waters 2777 Sample Manager, Installation and Maintenance Guide, 136 pages.
International Search Report for corresponding application No. PCT/US2006/046403 mailed Apr. 5, 2007.
International Search Report for corresponding application No. PCT/US2006/061804 mailed Jan. 22, 2008.
International Search Report for corresponding application No. PCT/US2005/020732 mailed Sep. 29, 2005.

* cited by examiner

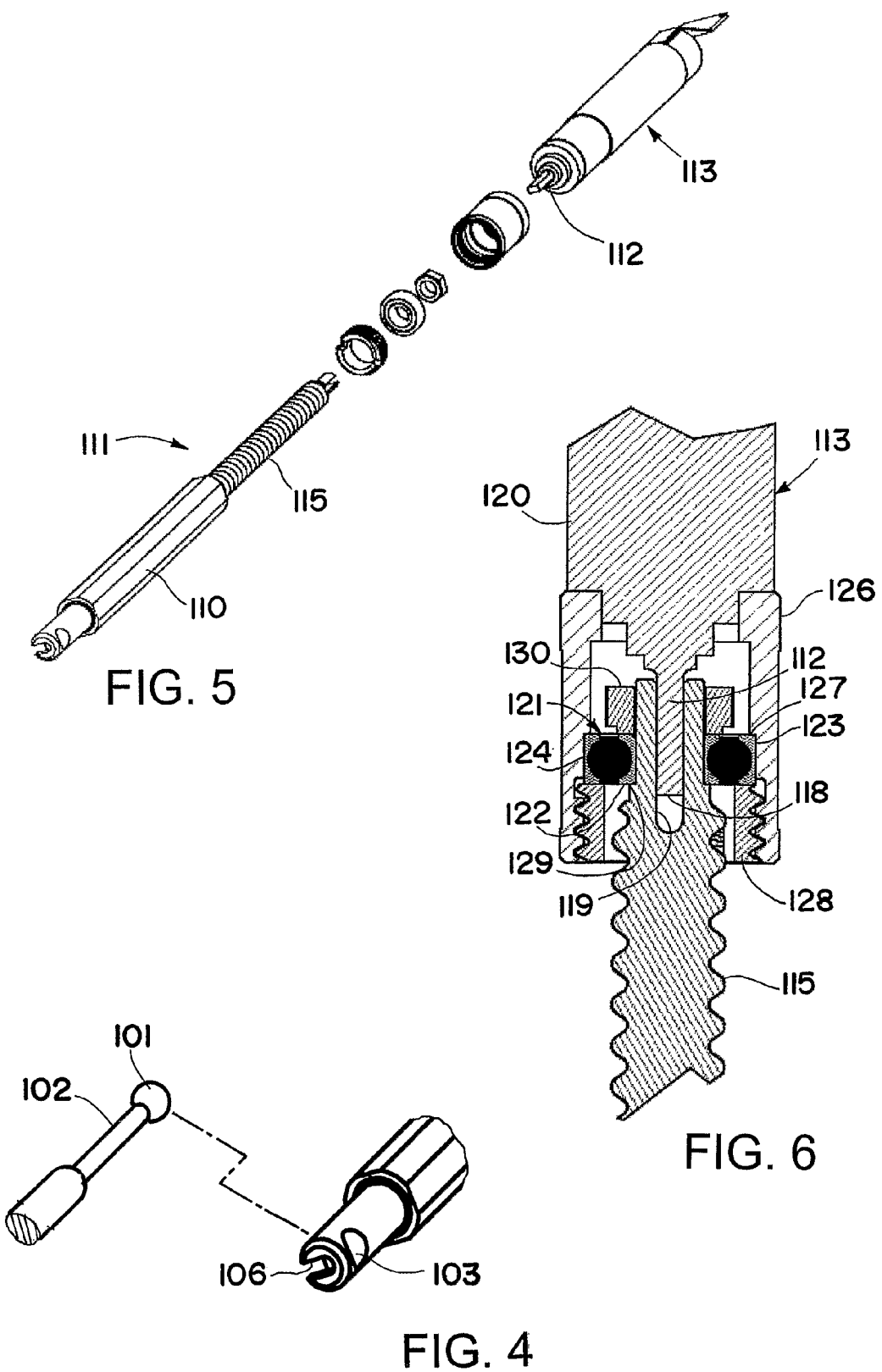

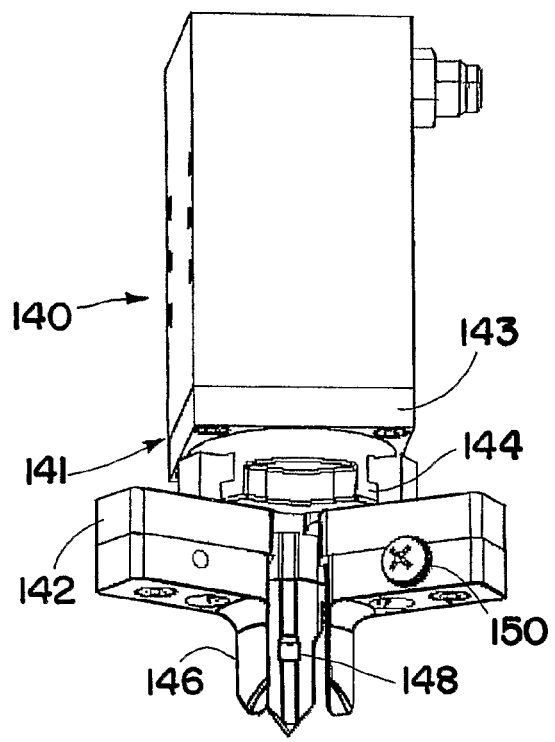
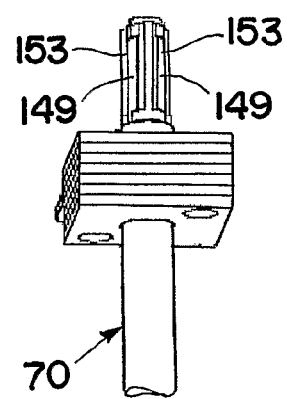
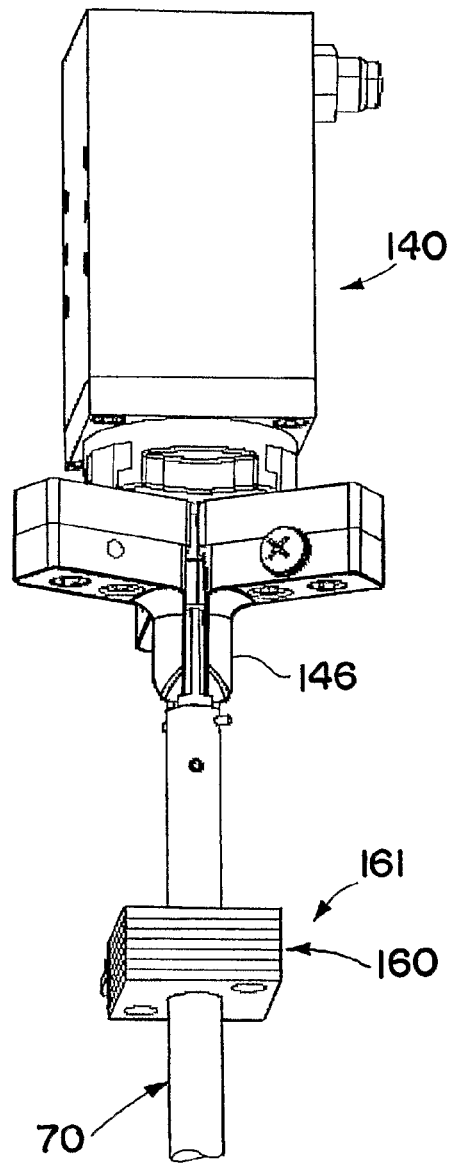
FIG. 7
FIG. 8

SAMPLING PROBE, GRIPPER AND INTERFACE FOR LABORATORY SAMPLE MANAGEMENT SYSTEMS

This application is a national phase of International Application No. PCT/US2006/002845, filed Jan. 27, 2006 and published in the English language under International Publication No. WO 2006/083695 A2.

RELATED APPLICATIONS

This application claims the benefit of U.S. Provisional Application No. 60/648,213 filed Jan. 28, 2005, and U.S. Provisional Application No. of the same title as above and filed Jan. 23, 2006, both of which are hereby incorporated herein by reference in their entireties.

FIELD OF THE INVENTION

The invention herein described relates generally to laboratory sample management operations and systems including robotic handling systems, components and methods, particularly for analytical applications, more particularly for liquid sample analytical systems, and still more particularly for bioanalytical and pharmaceutical applications.

BACKGROUND

Sample handling robots of various configurations are known in the biotechnology industry. A common feature of such systems is the use of a robotic or other motion control device to either move a fluid aspirating/-dispensing syringe (herein generally referred to as a sampling probe) about a deck of vessels or other deck components like wash stations, reagent troughs, injection valves, etc., or to move the vessels and/or other deck components relative to a stationary sampling probe. Among the more sophisticated systems, plural sampling probes are ganged together for common movement by a sample handler.

RELATED APPLICATION

International Publication No. WO 2005/124366 A1, which is hereby incorporated herein by reference, describes a system and method that enables efficient transport of movable devices such as sampling probes and other transportable devices. The system and method permit operational timesharing of a transport mechanism or multiple transport mechanisms for the movable devices. In addition, control of a transport mechanism can be effected on an event-driven basis. To facilitate system control, each movable device may be uniquely identified for independent operation by the controller.

The sampling probes typically provide for aspirating and/or dispensing an agent. The sampling probes may be self-contained thereby eliminating the need for a tether and thus reducing the complexity of coordinating the flow of the sampling probes through the system. An untethered self-contained sampling probe typically would include a plunger and a motive device for moving the plunger in response to a command signal. The command signal may be effected wirelessly between the sampling probe and a stationary system component, and/or by other suitable means.

The self-contained sampling probe may include a dedicated metering device for independent aspiration and/or dispensing of an agent, and control circuitry for receiving commands and controlling the metering device. The metering device generally comprises a syringe including a lumen, a plunger for drawing and/or dispensing a fluid into and/or from the lumen, and a motive device, such as an electric motor, for moving the plunger. In addition, the sampling probe may include a power supply for powering the motor and associated control circuitry, or other means by which power is supplied to the syringe at a station.

SUMMARY OF THE INVENTION

The present invention provides various improvements in sampling probes, syringe pumps, and related equipment, including improvements particularly applicable to a self-contained probe and associated devices that may be used in the above-described system and method, and which provides additional functionality to such systems.

According to one aspect of the invention, a sampling probe comprises a connector module, drive module and/or a syringe module, at least two of which are removably coupled coaxially to one another to allow for different modules to be interchangeably coupled together. The drive module and syringe module may be removably coupled by mating threads permitting the syringe module to be screwed onto and off of the drive module. In particular, the drive module and syringe module may include a drive module housing and a syringe module housing, respectively, the syringe module housing may form a continuation of the drive module housing when coupled thereto. The drive module may include a drive motor and a rotary-to-linear motion transfer device, and the syringe module includes a plunger configured at one end for detachable coupling to the rotary-to-linear motion transfer device. Preferably the coupling provides quick connection and disconnection.

According to another aspect of the invention, a syringe module for a sampling probe comprises a barrel, end members at opposite ends of the barrel, a dispensing/aspirating needle connected on one of the end members, and the other end member including a through hole for passage of the rod of a plunger disposed in the barrel for reciprocating movement. The plunger rod has at it distal end a coupler for quick connection to a coupling member of a drive module. The coupler may be an enlarged head, particularly a ball, on an end of the plunger rod.

According to still another aspect of the invention, a method for reconfiguring a sampling probe, comprises the steps of unscrewing a first syringe module including a plunger barrel from a drive module, and screwing onto the drive module a second syringe module. The second syringe module may include a barrel that has a capacity different from the capacity of the barrel of the first syringe module.

According to a further aspect of the invention, a sampling probe that can be moved into and out of engagement with an external device, comprises a housing, a plunger disposed within the housing, a motor operatively coupled to the plunger for moving the plunger for dispensing and/or aspirating a material, on-board electrical circuitry including one or more of a microcontroller, memory and motor control circuitry, and a connector assembly for connecting the electrical circuitry to the external device. The connector assembly includes at least one contact member located at a side wall of the housing for interfacing with at least one mating contact member of the external device. The sampling probe may be used in combination with the external device, the external device including a plurality of annular mating connectors disposed along a socket for receiving the sampling probe, the annular mating connectors having an axial spacing corresponding to the axial spacing of the plurality of contact members of the sampling probe.

According to a still further aspect of the invention, an interface device is provided for a sampling probe that includes a housing, a plunger disposed within the housing, a motor operatively coupled to the plunger for moving the plunger for dispensing and/or aspirating a material, on-board electrical circuitry including one or more of a microcontroller, memory and motor control circuitry, and a connector assembly for connecting the electrical circuitry to the external device, which connector assembly includes at least one contact member located at a side wall of the housing. The interface device includes an aperture for receiving the sampling probe, and at least one mating contact member for interfacing with the contact member of the connector assembly. The contacts and insulators may be formed by plates stacked on top of one another, and the plates may include a plurality of apertures for receiving and interfacing with a plurality of sampling probes.

According to another further aspect of the invention, an interface device is provided for a sampling probe that includes a housing, a plunger disposed within the housing, a motor operatively coupled to the plunger for moving the plunger for dispensing and/or aspirating a material, on-board electrical circuitry including one or more of a microcontroller, memory and motor control circuitry, and a connector assembly for connecting the electrical circuitry to the external device, which connector assembly includes at least one contact member located at the top aspect of the sampling probe. The interface device includes a gripper mechanism for receiving the sampling probe and which is connected electrically to an external device, and at least one mating contact member for interfacing with the contact member of the connector assembly.

According to yet another aspect of the invention, a sampling probe including a barrel, a plunger movable in the barrel for dispensing and/or aspirating a material, and an electronically readable identifier. The electronically readable identifier may include an RFID device or bar code. The electronically readable identifier may be configured to store at least one of barrel volume information, date of manufacture, and manufacturer certification.

According to another aspect of the invention, a sampling probe includes a barrel, a plunger movable in the barrel for dispensing and/or aspiration a material, a drive motor, and a ball and socket connection between the drive motor and plunger.

According to a further aspect of the invention, a drive assembly is provided for a sampling probe. The drive assembly comprises a housing having a center guide passage, an electric motor within the housing, a screw coaxially aligned with and coupled to the motor for rotation of the screw when the motor is operated, and a nut constrained in the center guide passage of the housing for linear movement, the nut having an outer surface rotationally interfering with an interior surface of the housing to prevent rotation of the nut relative to the housing while permitting axial movement of the nut in the center bore of the housing. The nut engages the screw such that rotation of the screw effects such axial movement of the nut in the center bore of the housing.

According to yet another aspect of the invention, a drive assembly for a sampling probe comprises a housing, an electric motor located within the housing and including a rotatable drive shaft, and a screw coaxially aligned with the motor, wherein the screw and rotatable drive shaft are drivingly coupled by a mating spade and slot members.

According to still another aspect of the invention, a drive assembly for a sampling probe comprises a housing, a motor assembly within the housing and including a rotating drive shaft, a screw coaxially aligned with and coupled to the rotating drive shaft for rotation of the screw when the motor assembly is operated, a nut constrained in the housing for linear movement, and a radial bearing including radially inner and out races rotatable relative to one another, the radially inner race being secured to an end of the screw against relative axial movement, and the radially outer race being secured to the housing against relative axial movement.

According to a still further aspect of the invention, a drive assembly for a sampling probe has a screw and rotatable drive shaft that are drivingly coupled by mating spade and slot members.

According to another aspect of the invention, a syringe module for a pumping device comprises a barrel, end members at opposite ends of the barrel, and a valve mechanism connected on one of the end members. The other end member includes a through hole for passage of the rod of a plunger disposed in the barrel for reciprocating movement. The valve mechanism has an inlet and outlet which may be connected to a liquid source and liquid receiver, respectively. The valve mechanism provides for fluid to be drawn from the inlet into the barrel when the plunger is retracted and for fluid to be pumped through the outlet when the plunger is extended. This may be effected, for example, through the use of check valves connected between the inlet and outlet and a chamber in the valve mechanism that is in communication with the interior chamber of the barrel.

Still other aspects of the invention are summarized as follows:

a sampling probe comprising a memory for onboard storage of audit information and/or operational instruction sets, and a communication device for effecting transfer of such audit information and/or operational instruction sets to and/or from an external device;

a self-contained sampling probe including a syringe barrel and a plunger drive, and wherein the probe is capable of pushing and drawing against several hundred psi;

a system comprising a self-contained sampling probe including electrical circuitry to which power, ground and communication contacts are coupled, and an external device including plural contacts for electrically connecting to the power, ground and communication contacts, and auto-sense circuitry for ascertaining which of the contacts of the external device are connected to the power, ground and communication contacts of the sampling probe when the sampling probe is engaged with the external device;

a system comprising at least one self-contained sampling probe, and a hand-held device to which the sampling probe or probes is/are connected and electrically interfaced; and a sampling probe comprising a drive module and a connector module removably coupled coaxially to the drive module to allow for replacement of one module with respect to the other module.

Further features of the invention will become apparent from the following detailed description when considered in conjunction with the drawings.

BRIEF DESCRIPTION OF THE DRAWINGS

In the annexed drawings,

FIG. 4 is an exploded fragmentary perspective view of a portion of the sampling probe of FIG. 3, illustrating an exemplary interconnection between a probe plunger and drive therefor;

FIG. 5 is an exploded perspective view of an exemplary plunger drive assembly employed in the sampling probe of FIG. 3;

FIG. 6 is a fragmentary cross-sectional view of the plunger drive assembly of FIG. 5 showing a drive coupling between the output shaft of a motor assembly and the screw of a rotary-to-linear motion conversion assembly;

FIG. 7 is a perspective view showing the sampling probe in association with an exemplary electrical probe interface and an exemplary gripper, with the gripper shown spaced from the sampling probe;

FIG. 8 is a perspective view similar to FIG. 7, showing the sampling probe being gripped by the gripper and partially withdrawn from the interface;

DETAILED DESCRIPTION

Because the invention was conceived and developed for use in an adaptive, synchronized motion and fluids system for automating the sample handling process associated with analytical processes and especially bioanalytical processes such as introducing samples into LC systems, HPLC systems, etc., it will be herein described chiefly in this context. However, the principles of the invention in their broader aspects can be adapted to other types of systems. For example, the sampling probe described herein can be implemented in conjunction with a hand-held device capable of programming each syringe from a local interface or from a PC connection (wired or wireless) to the hand-held device for general laboratory operations such as aliquoting samples, dilutions, performing bioanalytical reactions at point of use, being placed onto a sample injection device for sample introduction into LC or GC equipment, or other general laboratory operations. Another example includes placing several sampling probes in a hand-transportable grid-like element capable of programming each syringe in the grid from a local interface or from a PC connection (wired or wireless) to the grid wherein each syringe in the collection is instructed to perform parallel general laboratory operations such as aspirating, dispensing, aliquoting, dilution, reactions, being placed onto a sample injection device for sample introduction into LC or GC equipment, or other general laboratory operations. Sampling probes used in this manner can obviate transfers from container to container in as much as each probe serves as a container through several unit operations. In a practical sense, collections of probes can be handed from lab to lab or group to group for continued use throughout a sample's workflow. This has the benefit of reducing the number of surfaces with which the sample comes in contact and thus reduces sample loss commensurate with adsorption of sample molecule to such surfaces.

Figure 1:
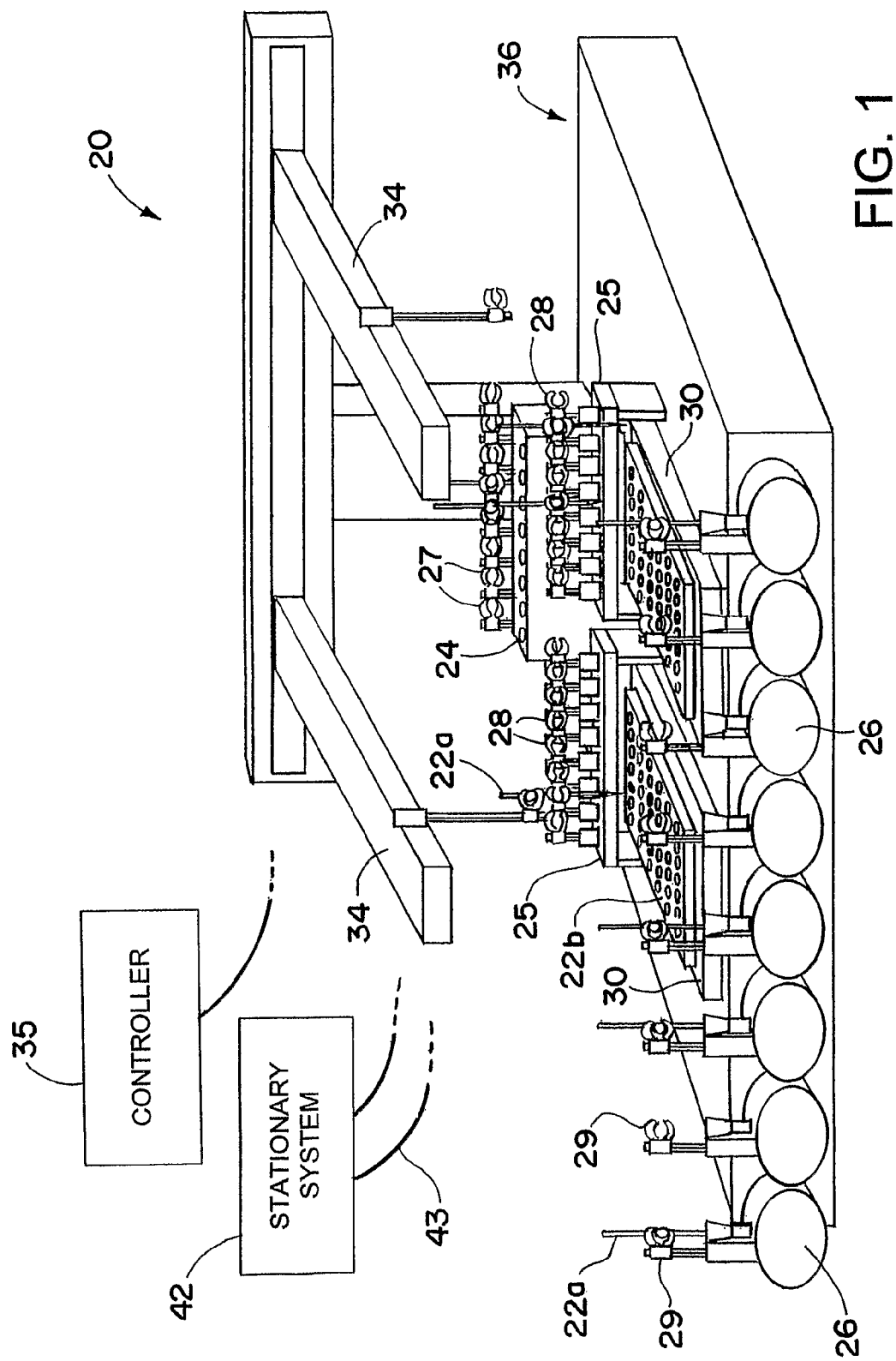
FIG. 1 is a schematic illustration of an exemplary embodiment of an analytical system.

Referring now in detail to the drawings and initially to FIG. 1, an exemplary embodiment of an analytical system is generally denoted by reference numeral 20. The system 20 comprises one or more movable devices 22 for use in the performance of one or more analytical operations, which movable devices may be active devices, such as sampling probes 22a, and/or passive devices, such as trays 22b.

The system further comprises one or more stations which, as shown, may be arranged in groups. For example, the system 20 includes one or more wash stations 24, one or more aspirating stations 25 (two shown), and one or more analysis stations 26. The stations 24, 25 and 26 have respectively associated therewith one or more receivers 27, 28 and 29 for receiving one or more of the movable devices 22a so that a prescribed operation can be commenced at the respective station. The stations 25 also are provided with a receiver 30 for the trays 22b.

The system further comprises one or more transport mechanisms 34 for transporting the movable devices 22 from station to station, and a controller 35 for directing the transport mechanism to leave at least one of the movable devices with the receiver(s) in a first one of the stations thereby to free the transport mechanism for transport of at least one other movable device between stations while the movable device or devices left at the first station are used to perform a prescribed operation at the first station. Simply, the moveable devices are transported to and among receivers via the transport mechanism. Once transported, the moveable devices are "released" to the receivers by the transport mechanism, thereby freeing the transport mechanism for transporting other moveable devices between the stations.

In the illustrated embodiment, the stations are arranged in relation to what is commonly referred to a "deck" 36.

As a result of the foregoing arrangement, many operations can be executed in parallel, thereby increasing overall system efficiency and throughput relative to the prior art systems where the movable device remains attached to the transport mechanism for effecting an operation. The movable devices 22, and particularly the active movable devices 22a, can be positioned anywhere in the system without constraint on other movable devices, active or passive.

The transport mechanisms 34 can be, but are not limited to, robots, particularly robotic devices capable of three-dimensional translating (X, Y and Z axis) and/or rotational movement; levitation devices; antigravity devices; automated slides or tracks; stackers; and human beings. The transport mechanisms can be equipped with a suitable holder for the movable device being transported. As will be appreciated, multiple transport mechanisms may be employed and independently operated to retrieve and transport the movable devices. In addition, the movable devices may be transported by attending personnel, as in response to instructions provided by controller either audibly, visually and/or otherwise.

The movable devices 22 can be, but are not limited to, sampling probes/syringes; reaction vessels; plate carriers; sample loops; and other active or passive devices. An active movable device is one that is capable of performing an action, such as a syringe that can aspirate or dispense an agent. A passive movable device is one that does not perform an action but which can receive or be subjected to an action, such as a vial containing a sample or a tray containing multiple samples. An otherwise passive movable device may become an active or intelligent movable device if it is equipped with logic circuitry for storing a workflow and communicating a need for a particular service with the system controller or other system components.

The stations can be, but are not limited to, wash stations; aspirating and/or dispensing stations, sample reformatting stations; reagent addition stations; dilution stations; shaking stations; thermally and environmentally controlled stations; parking stations; plate handlers; centrifuges; and other processing stations. At any given station multiple processes may be performed, as desired for a particular application. The stations may be equipped with positioning devices for positioning components relative to other components.

Moreover, the stations may be logically grouped in clusters, and the movable devices may be transported between clusters of stations throughout a lab-wide or corporate-wide set of clusters. A cluster of stations may be configured, for example, as an autosampler system or a generic liquid handling system. A cluster of stations is one that is grouped for a particular purpose. FIG. 1 illustrates one such cluster of stations that functions as an autosampler system.

The receivers 27-30 at the respective stations can be, but are not limited to, grippers; holders; cradles; electrical and/or mechanical grid systems; manipulators; or other components. The receivers may physically articulate with the movable device delivered thereto and position it for proper operation.

As will be appreciated, the transport mechanism(s) 34 can be a low precision device(s) inasmuch as any high precision positioning needed at a station can be obtained by the receiver or receivers which can include a high precision positioning and/or operationally capable device.

One or more of the receivers 27-30 may possess the ability to assist the movable component received thereby in the performance of a requisite task at the respective station. For example, the receivers 27 at the wash station 24 may have the capability of raising and lowering a movable device, particularly a sampling probe 22a, into and out of a wash well or trough. Other receiver actions may include not only up and down actuation but also rotation, precise servo driven multi-axis positioning, and others. For example, the receivers 30 for the stations 25 may include a high precision X and Y positioning device used for fine positioning of microplates under sampling probes 22a held in the stations 25.

Figure 2:
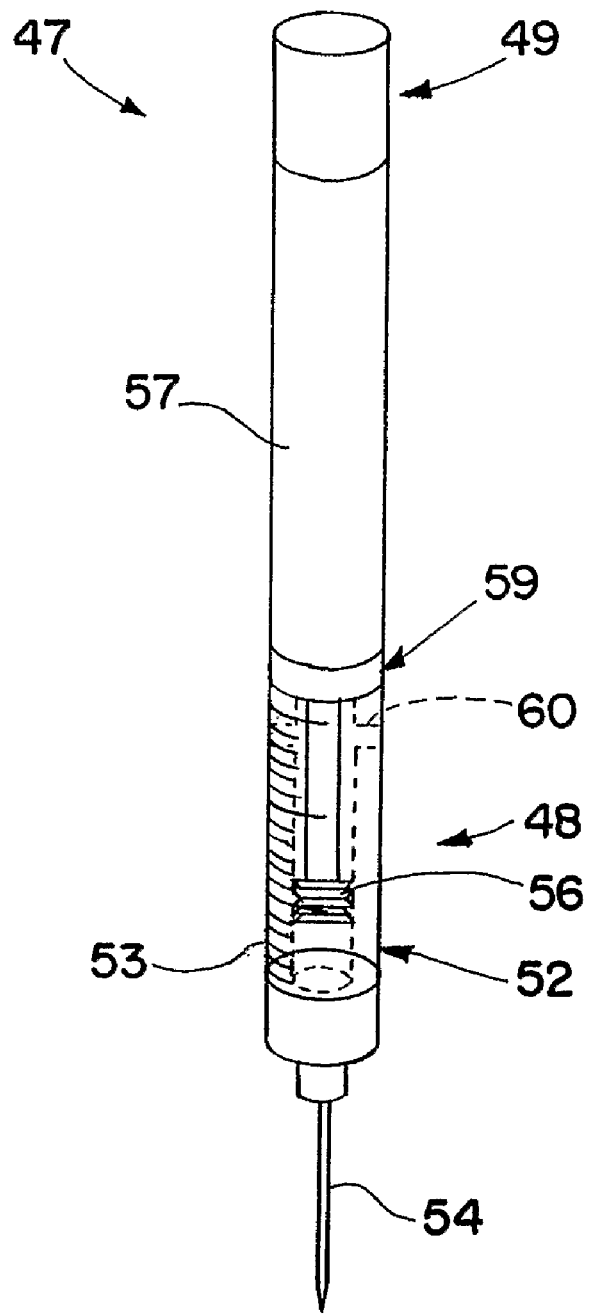
FIG. 2 is an illustration of an exemplary self-contained sampling probe useful in the analytical system of FIG. 1.

The movable devices 22 may include one or more sampling probes (e.g. syringes or pipettes) for aspirating and/or dispensing an agent. An exemplary untethered self-contained sampling probe is denoted by reference numeral 47 in FIG. 2. The probe 47 may include a dedicated metering device 48 for independent aspiration and/or dispensing of an agent, and control circuitry 49 for communicating with the overall system controller 35 (or components thereof) and for controlling the metering device. The metering device may include a syringe 52 including a syringe barrel 53 terminating at a lumen (e.g. needle) 54, a plunger 56 movable in the barrel for drawing and/or dispensing a fluid into and/or from the barrel via the lumen, and a motive device 57, such as an electric motor, for moving the plunger via an appropriate gear train or other transmission components. In addition, the sampling probe 47 may include a power supply 59 for powering the motor and associated control circuitry, or other means by which power is supplied to the syringe at a station. Command signals may be communicated wirelessly between the sampling probe and system controller (or components thereof), or by a make and break signal connection at point of placement (physical electrical contact or inductive), clip on control circuitry, and/or by other suitable means.

The probes may contain a time of day clock and may be used for timed reactions. For example, the probe may automatically draw up a plurality of solutions, mix them in its barrel, and hold them for a designated amount of time before expelling them. It may also automatically draw up a solution or solutions, wirelessly tell the controller 35 to inform the user to place the syringe in a laboratory device or container separate from its current location (e.g. incubator or refrigerator), sit in the device or container for a designated amount of time, and wirelessly tell the controller to tell the user to remove it from the device or container so it can become part of the active system again.

The syringe barrel may also have a cross-port 60 allowing for fast washing once the plunger is fully retracted.

An analytical system, such as that described above, can be operated in an "event driven" or time-based mode, the event driven mode being the preferred embodiment. In addition to permitting operational timesharing among all transportable devices associated with a given system, attention to each device can be provided on an as needed basis with the transportable device itself requesting service as an "event" in a system queue maintained by the controller. In this context, a system could consist of a single instrument tasked with performing a prescribed set of functions but employing multiple transportable devices. Alternatively, the system could include a network of instruments (each employing multiple transportable devices) deployed as part of an enterprise-wide laboratory, facility or corporate automation entity.

Accordingly, active movable components may request service at the appropriate point within their current workflow and the system controller and/or other components of the system can respond to that request. This framework can be extended to include not only transport control but any servicing the active movable components on an event driven basis. For example, a system's movable elements might share an electrical discharge device or a heating device whose services are requested on an as needed basis. The requests are non-deterministic in nature as they are issued in accordance with each movable component's workflow requirement for such service at such time that it is needed. Another example is in regard to each movable device's service and maintenance schedule. Each device can request service in an event driven manner to the cluster to which it is currently interacting.

According to one particular paradigm, the controller (or dedicated components thereof such as a transport controller) need not know a priori or deterministically which movable devices will require transport at any given time. Instead, the movable devices can be configured to request service at the appropriate point within their current workflow and the transport mechanism commanded in response to that request.

As may be desired, each movable device may be uniquely identifiable within its control logic to allow control transmissions to reach a specific device on a "hub" via a "broadcast" transmission scheme.

Figure 3:
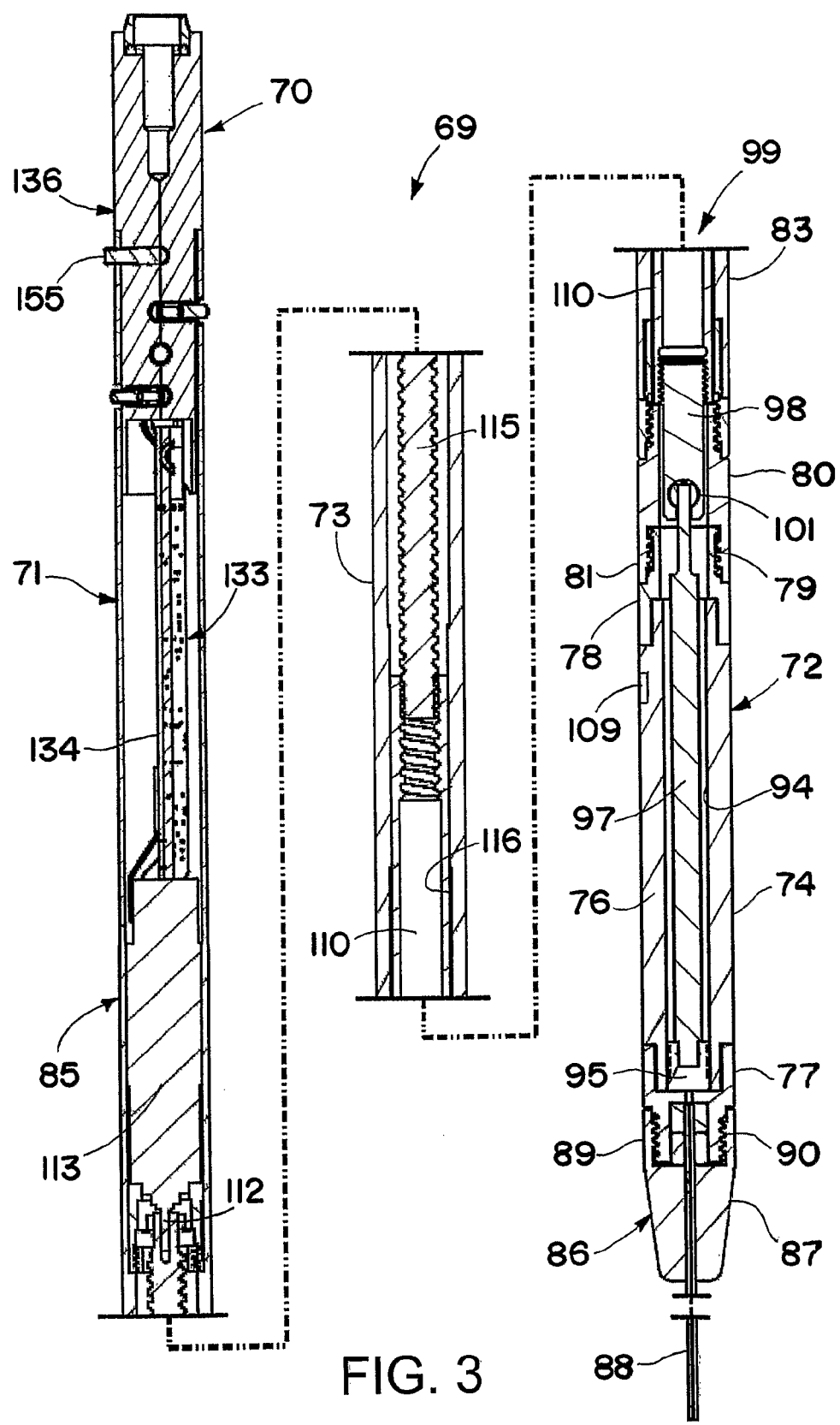
FIG. 3 is a cross-sectional view of an exemplary sampling probe according to the present invention, which probe comprises connector, drive and syringe modules.

Referring now to FIG. 3, an exemplary self-contained sampling probe according to the present invention is indicated generally by reference numeral 69. The sampling probe generally comprises a connector module 70, a drive module 71 and a syringe module 72 removably coupled coaxially to the drive module to allow for different syringe modules to be interchangeably coupled to the drive module. This allows, for example, replacement of second syringe modules including barrels having different capacities or to replace broken or leaking barrels.

The probe modules 70-72 may be interconnected by any suitable means that preferably allows for quick and easy replacement of one module for another. In the illustrated sampling probe, the drive and syringe modules are removably coupled by mating threads, thereby permitting the syringe module to be screwed onto and off of the drive module. The connector and drive modules are removably coupled by a sleeve and pin connection. Although screw and sleeve/pin connections are shown, other types of connections may be used to removably interconnect the drive and syringe module housings, such as quarter turn locking connections, ball and socket connections (like those to hold sockets onto ratchets), "U" nuts, wedge pins, Swage connections, or set screws.

More particularly, the drive module 71 and syringe module 72 respectively include a drive module housing 73 and a syringe module housing 74, each forming an axial continuation of the other. The syringe module housing includes a transparent or translucent plunger barrel 76, an outer end piece 77 at the axially outer end of the barrel, and an inner end piece 78 at the axially inner end of the barrel. The inner end piece 78 has a reduced diameter, externally threaded end portion 79 that is threaded into a counterbored, internally threaded axially inner end portion 81 of an end sleeve member 80 used to connect to the end of the drive module housing 73. The end sleeve member 80 is screw-connected to a main tubular body portion 83 of the drive module housing 73.

The module housings 71 and 72 preferably are cylindrical with the outer surfaces thereof having for the most part the same outer diameter such that together the housings form a probe housing 85 having a substantially continuous cylindrical outer surface of uniform diameter. In a preferred embodiment, the maximum outer diameter of the probe housing 75 is equal or less than 9 mm so that the sampling probes can be ganged together or individually placed next to each other dynamically during operation as in a grid pattern at a 9 mm center-to-center spacing, or less.

The outer end piece 77 of the syringe module housing 72 has fastened thereto a needle assembly 86 including a needle support body 87 that supports a needle 88 (e.g. any suitable lumen). The needle support body 87, which may be tapered as shown in FIG. 3, has an internally threaded inner end portion 89 screwed onto a reduced diameter, externally threaded end portion 90 of the outer barrel end piece 77. The taper serves as a lead-in to the receiving elements during placement of the syringe as well as helping to reduce the chance of scoring or shearing the sealing material present in some of the receiving elements. The screw-on connection means (or other suitable means) allows for easy interchange of different needle assemblies as needed. It also allows for connection of other elements such as valves to allow the syringe to be used as a syringe pump. The needle assemblies may have different length and/or diameter needles for different applications, as well as different types of needles.

The needle support body 87 includes a central passage for the needle 88 that protrudes from the outer end of the needle support body. The inner end of the needle, which may be provided with a larger diameter collar, may be secured within a recess in the end portion 90 of the outer barrel end piece 77 by the needle support body. The inner end of the needle may be sealed by a Teflon face seal to the bottom wall of the recess that includes a center passage providing for fluid communication between the end of the needle and the interior of the barrel 76.

The barrel 76 has a cylindrical interior chamber 94 in which a plunger 95 moves axially for dispensing and/or aspirating a fluid from and/or into the chamber 94. The plunger and barrel may be of a conventional construction that provides for a fluid tight seal between the plunger and barrel while allowing axial movement of the plunger in the barrel.

The plunger 95 is connected to the end of a plunger rod 97 that connects the plunger to an axially movable drive coupling 98 of a plunger drive assembly 99 included in the drive module 71. While any suitable type of connection may be used, preferably a ball and socket connection is provided to accommodate any misalignment between the plunger rod and an axially driven coupling of the drive assembly. More particularly, the joint may be a miniature universal joint that ensures freedom of limited angular movement while maintaining axial stiffness with no relative axial motion. Also, a quick connect/disconnect connection is provided between the plunger rod and drive coupling to facilitate quick and easy connection and disconnection of the syringe module and drive module.

In the illustrated embodiment and as shown in FIGS. 3 and 4, the coupling between the plunger rod 97 and drive coupling 98 is effected by an enlarged head 101 at the end of a reduced width/diameter neck or stem 102 at the inner end of the plunger rod and a socket 103 in the drive coupling 98. The head 101 preferably is ball-shape and sized for a close fit within the socket 103, so that there is essentially no axial play between the plunger rod and drive coupling, while still allowing limited angular movement of the plunger rod relative to the drive coupling. A keyhole slot 106 is provided in the side of the drive coupling 98 to allow the ball and stem to be inserted laterally into the drive coupling for seating of the ball 101 in the socket.

To connect the plunger rod 97 to the drive coupling 98, the plunger rod may be partially withdrawn from the syringe module housing 74 to allow the plunger rod to be grasped and manipulated. The ball 101 and stem 102 may then be inserted through the keyhole slot 106 to connect the plunger rod to the drive coupling. Once connected, the housing of the syringe module may be screwed onto the housing of the drive module.

In view of the foregoing, the sampling probe 69 can be easily reconfigured by simply unscrewing a first syringe module including a plunger barrel from a drive module, and screwing onto the drive module a second syringe module. Typically the plunger will be provided in the syringe modules for replacement along with the syringe barrels.

As depicted in FIG. 3, the syringe module 72 may be provided with an electronically readable identifier 109, such as a bar code or RFID device. The electronically readable identifier may be configured to store, for example, at least one of barrel volume information, date of manufacture, manufacturer certification, serialization information, location of manufacture, and specific calibration information as needed. The RFID or other identifier device may be located in or on the syringe module at any suitable location. Although an RFID device is shown seated in a recess in the side wall of the barrel, the RFID device, by way of further example, may be located in or on the sleeve 80 which may be made of a plastic material so as not to interfere with the function of the RFID device, whereas the barrel end pieces may be made of metal, such as stainless steel. The barrel will typically be made of glass or a plastic material that preferably is transparent or translucent.

As shown in FIGS. 3 and 5, the drive coupling 98 in the illustrated embodiment is attached to (but may be formed integrally with) the nut 110 of a lead screw and nut assembly 111 that is used to convert rotary motion of an output shaft 112 of a drive motor assembly 113 to linear motion of the nut. As shown, the nut 110 is a tubular member that is internally threaded to receive an externally threaded end of the drive coupling 98 which extends coaxially from the end of the nut. The nut also is internally threaded for driving engagement with a rotatable lead screw 115. As will be appreciated, rotation of the screw in one direction will move the nut axially in one direction and rotation of the screw in the opposite direction will move the nut axially in the opposite direction. The nut is guided for such linear axial movement in a guide passage 116 in the drive module housing 73. Although other types of anti-rotation devices may be used, in the illustrated embodiment the nut and guide passage have corresponding non-circular cross-sections for preventing rotation of the nut relative to the housing while permitting axial movement of the nut in the center bore of the housing. For example, the nut and guide passage may be octagonal in cross-section as shown.

Referring to FIGS. 5 and 6, the output shaft 112 of the drive motor assembly is coupled to the lead screw 115 by mating spade and slot members 118 and 119. As shown, the spade member 118 is formed by the end of the output shaft and the slot member 119 is formed by the end of the screw 115. The spade is sized to closely fit in the slot of the slot member to provide for essentially no angular relative movement (zero rotational slip) while providing for axial movement between the drive shaft and screw that assists in avoiding axial reactionary loads from passing from the screw to the drive motor assembly. This enables usage of small radius drive motor assemblies that may contain reduction gears or other components that cannot tolerate the anticipated axial loads acting on the screw.

In the illustrated embodiment, the axial loads are carried by a housing 120 enclosing an electric motor and gear reduction components of the motor assembly 113. This may be effected, for example, by way of a unique usage of a radial bearing 121. As best shown in FIG. 6, the radial bearing 121 includes radially inner and out races 122 and 123 that are rotatable relative to one another. A ball bearing may be employed and thus the races retain therebetween a plurality of balls 124. The radially inner race is secured to an end of the screw 115 against relative axial movement, and the radially outer race is secured to the housing 120 against relative axial movement via a tubular collar 126. That is, the outer and inner races are secured against axial movement independently of the drive shaft 112 to prevent axial loads from being transferred to the drive shaft. The dual race radial bearing thus functions as a thrust bearing. The bearing also radially supports the end of the lead screw while allowing free rotation of the screw. The outer race is retained in the collar 126 between an axially outwardly facing shoulder 127 and a nut 128 threaded into the collar. The inner race is retained on the slotted end of the screw between an axially inwardly facing shoulder 129 and a retainer 130 attached by suitable means to the screw, such as by screwing onto the screw end or by bonding using a suitable adhesive. The foregoing reduction of reactionary loads away from the motor assembly enables the probe (syringe) to puncture, push and/or draw against several hundred psi.

As above mentioned, the motor assembly 113 includes an electric rotary motor that typically will be provided with a speed reducer. The motor and speed reducer may be assembled in the housing 120 to which the connection collar 126 is attached as shown in FIG. 6. The motor and speed reducer may be of a conventional construction; such units being commercially available. The motor and speed reducer assembly is selected such that the outer diameter thereof allows for assembly of the drive unit in the housing of the drive module as seen in FIG. 3.

Figure 3A:
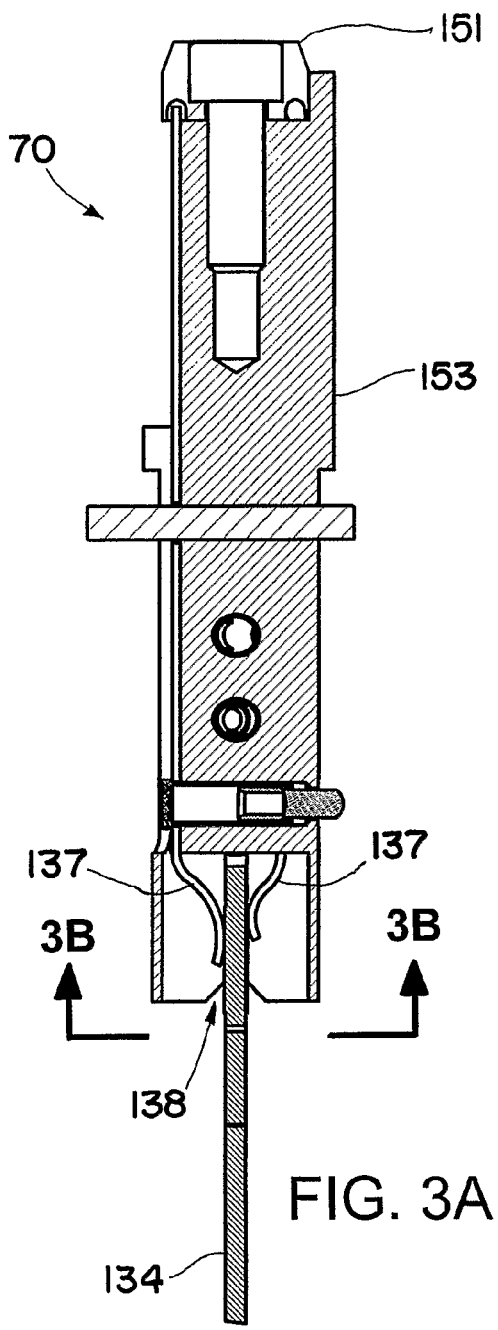
FIG. 3A is an enlarged cross-sectional view of a connector module forming part of the sampling probe of FIG. 3, showing the manner of its electrical connection to a printed circuit board in the drive module.
Figure 3B:
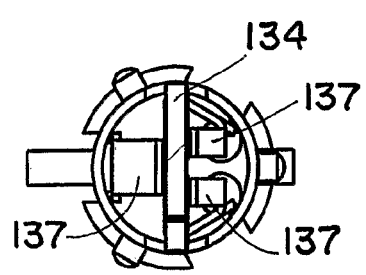
FIG. 3B is a view of the connector module and printed circuit board taken along the line 3B-3B of FIG. 3A.
Figure 3C:
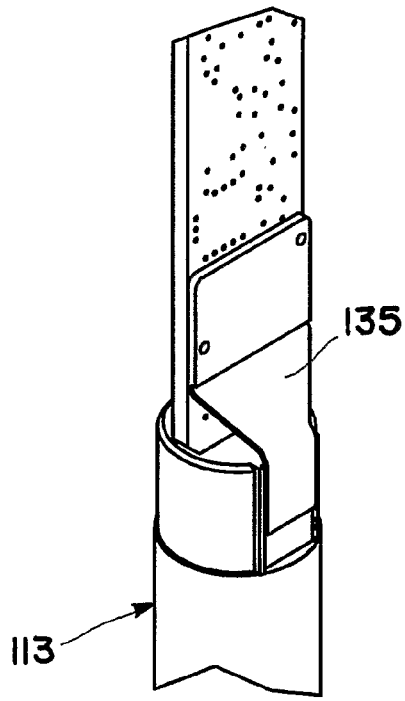
FIG. 3C is a fragmentary perspective view showing the electrical connection between the drive motor and printed circuit board of the drive module.

Referring to FIGS. 3 and 3A-3C, the motor assembly 113 is controlled by motor control circuitry 133 provided, for example, on a circuit board 134 suitably electrically connected to the motor of the motor assembly (such as by a flexible printed circuit connector 135 in the manner shown in FIG. 3C) and secured in the drive module housing by a potting compound (e.g. a thermally conductive, electrically isolating epoxy) or other suitable means. As shown, the circuit board may be assembled in the drive module in axial alignment with the motor assembly 113. The circuit board 134 also is connected to a connector assembly 136 in the connector module 70 for connecting the electrical circuitry to an external device or devices. In order to allow for removable connection of the connector module to the drive module, and as shown in FIGS. 3A and 3B, the connector module includes resilient tab contacts 137 disposed on opposite sides of a slot 138 into which the printed circuit board is inserted when the inner end of the connector module 70 is axially inserted into a socket end portion of the drive module. The tab contacts are free to flex when the board is inserted therebetween. The board has contact pads that are engaged by the contact tabs to effect electrical connection between the connector module and the drive module.

Figure 9:
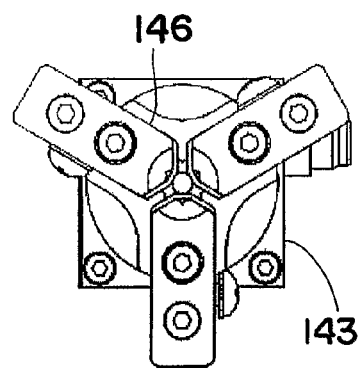
FIG. 9 is an end view of the gripper showing gripper jaws in a fully retracted (closed) position.
Figure 10:
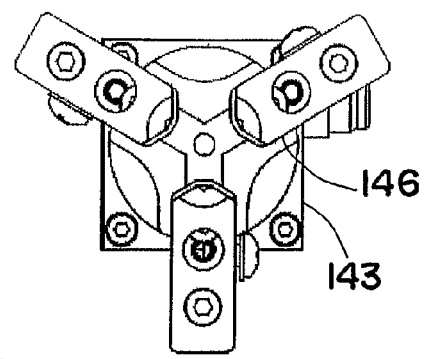
FIG. 10 is an end view similar to FIG. 9, showing the gripper jaws in a fully expanded (open) position.

Referring now to FIGS. 7 and 8, the therein illustrated probe holder is a probe gripper 140. The gripper 140 typically would be part of a transport mechanism used to transport the sampling probes from one location to another. The illustrated exemplary gripper includes a conventional electric three-jaw gripper assembly 141 that includes three radially movable jaws 142 mounted to a gripper body 143 which includes the jaw tracks 144, drives and controls for operating the gripper, i.e, moving the jaws between open and closed position. In FIGS. 7 and 9, the jaws are shown fully radially expanded and in FIGS. 8 and 10 the jaws are shown radially retracted.

The jaws 142 have attached thereto respective gripper fingers 146 for engaging and electrically interfacing with an upper gripping end portion of the sampling probe 69. The fingers 146 are configured such that when closed around the upper gripping portion of the sampling probe 69, the fingers will firmly engage and hold the sampling probe coaxially with the center of the chuck formed by the jaws. In addition, each finger 146 is provided with an electrical contact 148 for making electrical connection with a respective mating contact 149 on the sampling probe. As discussed further below, the fingers may taper going radially inwardly for engaging in correspondingly tapered grooves in the body of the connector module. In the event the fingers are not angularly centered relative to the grooves, the tapers may functions as cam surfaces causing the sampling probe to rotate relative to the gripper to bring the fingers into angularly centered alignment with the groove. The may be accomplished other ways, including other multifaceted configurations of the fingers and grooves, and other configurations of the gripper and connector probe.

In the illustrated embodiment, the mating contacts 149 on the sampling probe are circumferentially equally spaced around the upper end portion of the sampling probe, each electrically isolated with respect to one another and electrically connected to the electrical circuitry in the sampling probe. The electrical contacts 148 on the fingers are connected to the overall system controller by suitable means. To this end, the gripper fingers may each be provided with a terminal screw 150 for connection of a lead to the electrical contact of the gripper finger. The contacts 149 may be formed by contact bars. The inner ends of the bars may form the above-mentioned contact tabs 137, and the outer ends of the bars may be held in place by engagement in slots formed on the underside of the head of a fastener 151 attached to the outer end of the connector body 153 as shown in FIG. 3A.

The number of contacts and/or fingers can be varied as desired for a given application. For example, each finger 146 may include one or more contacts for mating respective contacts on the sampling probe which may be arranged in a variety of ways, such as circumferentially as shown and/or axially. In the illustrated embodiment, three contacts are provided, one for ground, one for power, and one for communication between the probe 69 and gripper 140.

In the illustrated embodiment, a specific contact on the gripper need not make contact with a specific contact on the probe, although this could be done since the angular positions of the probe and gripper can be tracked and maintained. Instead, the gripper has associated therewith electrical circuitry that electronically compensates for the alignment of the gripper with the contacts on the probe. When contact is made between the gripper and probe, an auto-sense procedure is performed whereby the determination is made as to which contacts of the gripper are in contact with the power, ground and signal contacts of the probe. After that, power can be supplied to the probe and communication effected with the probe.

Accordingly, whenever the probe is engaged by the gripper, communication can be established with the connector whereby sets of operational instructions can be downloaded to the probe, audit logs/status information can be uploaded from the probe, and operations such as pulling in or removing air gaps between liquids can be accomplished while the probe is in transit by the transport mechanism all further enhancing overall system throughput performance. Connections through the gripper are also desired when the syringe is used in conjunction with a hand-held device, such as a hand-held controller. The hand-held controller contains a gripper-like element into which the syringe is attached for stability, power, and communication with the hand-held processor. At the same time, a battery or other power storage device in the probe may be recharged, if desired.

In the illustrated embodiment, the connector module 70 includes a connector housing or body 153 that is connected to the drive module housing preferably in a manner that enables quick and easy removal and installation of the connector module. In the illustrated embodiment, the connector body has a cylindrical lower portion that is sized to fit telescopically into the end of the tubular body portion 83 of the drive module housing 73. The connector body may be secured, preferably releaseably, in the body portion 83, such as by means of a pin 155 extending through aligned radial holes in the tubular body portion 83 and the connector body 153. As discussed below, the pin 155 may also function as a locating key.

The upper portion of the connector body 153 preferably forms an axial extension of the drive module housing. In particular, the connector body has a maximum width about equal the width of the drive module housing.

Figure 12:
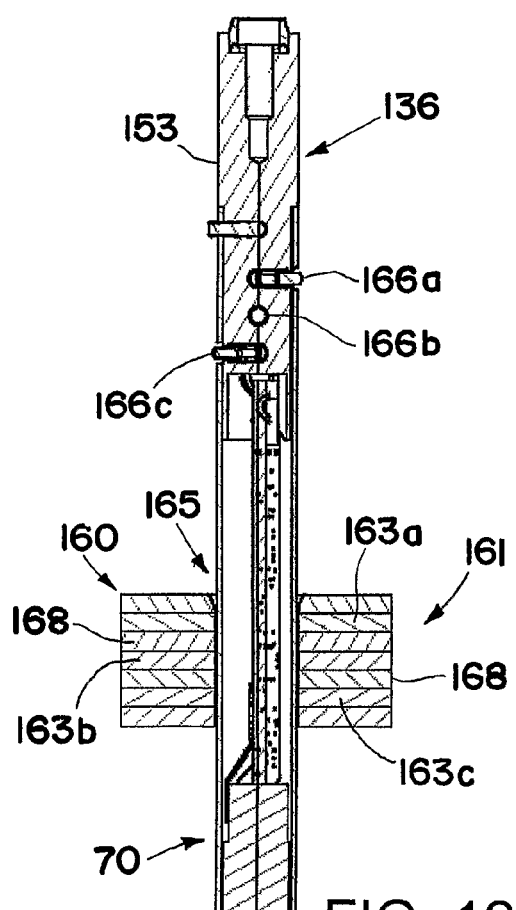
FIG. 12 is a cross-sectional view of the sampling probe and electrical interface showing details of the electrical components for effecting communication between the sampling probe and electrical interface.
Figure 13:
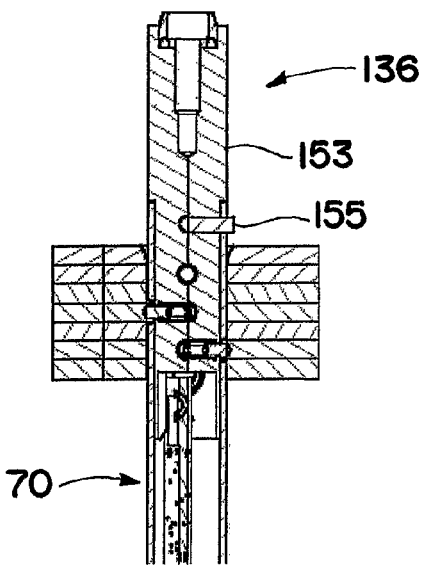
FIG. 13 is a cross-sectional view similar to FIG. 12, but showing the sampling probe fully seated in the electrical interface.
Figure 14:
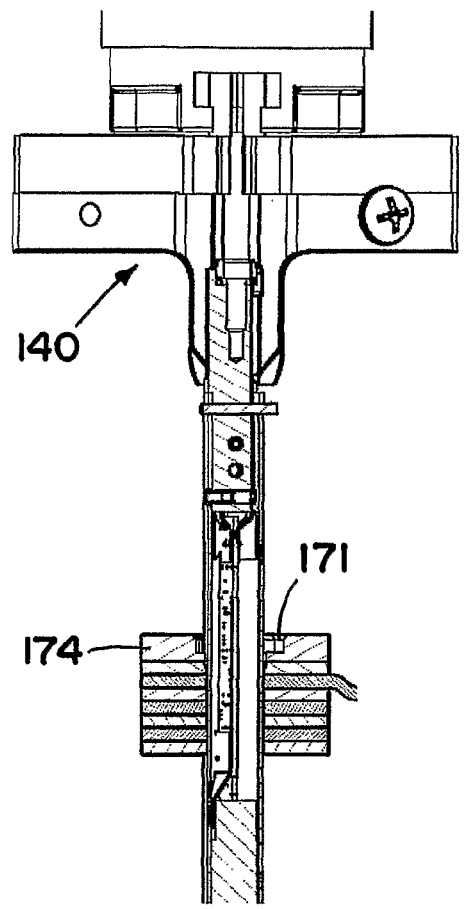
FIG. 14 is a part elevational, part cross-sectional view showing the sampling probe being inserted by the gripper into the electrical probe interface.
Figure 15:
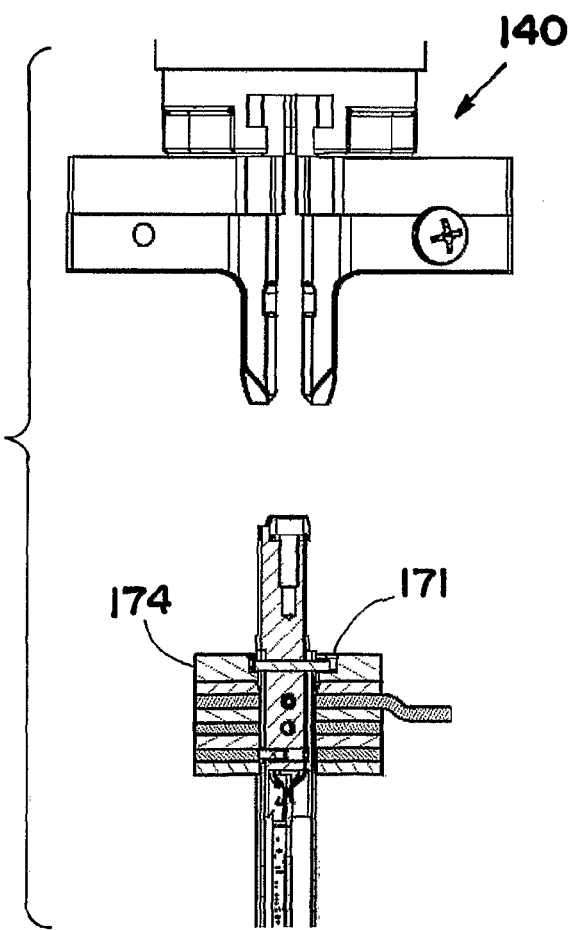
FIG. 15 is a part elevational, part cross-sectional view similar to FIG. 14, showing the sampling probe fully inserted into the probe interface and released from the gripper.
Figure 16:
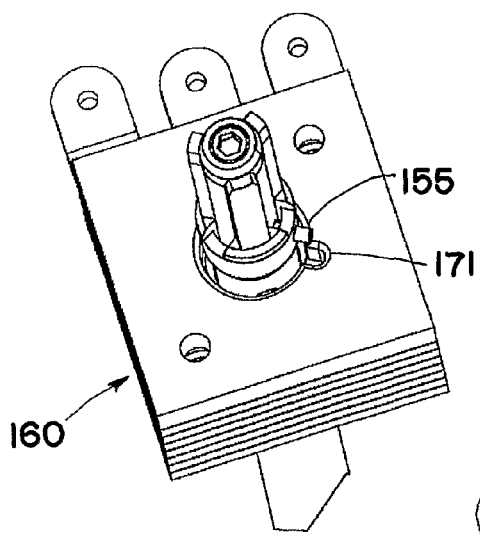
FIG. 16 is a perspective view showing sampling probe just prior to being fully inserted into the probe interface with gripper facets and electrical connections recessed about the circumference of the top portion of the probe.
Figure 17:
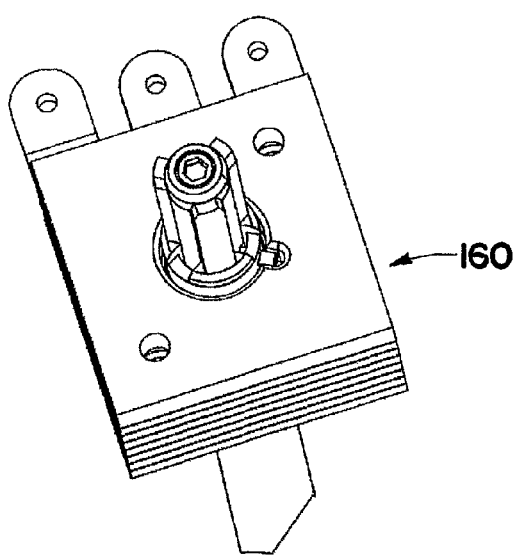
FIG. 17 is a perspective view similar to FIG. 16 showing sampling probe fully inserted into the probe interface with gripper facets and electrical connections recessed about the circumference of the top portion of the probe.

As shown in FIGS. 12 and 13, the connector body 153 extends above the end of the module housing to form a gripping end portion of the sampling probe 69. As shown in FIGS. 7 and 8, the connector body has circumferentially equally spaced apart gripper recesses 154 in which respective contacts 148 are located and exposed for contact with a finger contact 148 of the gripper 140 when the latter is closed around the upper end portion of the connector body. The fingers 146 preferably engage the connector body over an extended length for lateral stability and the fingers are engaged (seated) in the recesses 154 for rotational stability during movement.

As above mentioned, the gripper 140 may be used to move the probe 69 from position to position. For example, the gripper may be used to move the probe into and out of an interface device 160 that may form or be a part of a probe holder 161. The holder with the interface device may be provided at any one of the various stations between which the probe is transferred in the course of performing analytical-related or other functions. As shown in FIGS. 12 and 13, the interface device may include a plurality of annular mating contacts 163$a$-$c$ at a socket 165 or other aperture that receives the sampling probe, and the probe may include contacts 166$a$-$c$ for interfacing with the contacts 163$a$-$c$ of the interface device.

In the illustrated embodiment, the contact or contact members 166$a$-$c$ are located at different axial positions along the length of the sampling probe 69 for connection to respective contacts or contact members 163$a$-$c$ that are formed by respective conductive layers of the interface device. The conductive layers provide annular contact surfaces surrounding the aperture for effecting contact with the contact members 166$a$-$c$ of the connector assembly in any relatively rotated position thereof. The contact members 163$a$-$c$ may be conductive layers axially interleaved with a plurality of insulating layers 168 electrically isolating the conductive layers from one another. In particular, the contacts and insulators may be formed by plates stacked one top of one another. The contact plates may be connected to respective terminals 169

Figure 11:
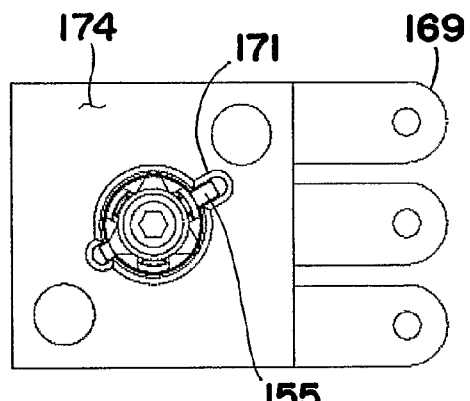
FIG. 11 is an end view of the sampling probe registered in the electrical interface.

(FIG. 11) used for connecting the interface to other electrical components, such as the system controller.

As shown in FIG. 13, the axial spacing of the contact members 163a-c corresponds to the axial spacing of the contact members 166a-c of the sampling probe, whereupon electrical contact will be effected therebetween when the sampling probe if fully seated/inserted into the socket of the interface device (brought into registry).

As shown in FIGS. 3, 12 and 13, the contact members 166a-c of the probe may be resiliently biased plunger contact members (pogo pins) that extend through and protrude from the side wall of the drive module housing 71. The housing has at the connector end thereof a tubular shell, and the connector body 153 closes the end of the tubular shell. The inner ends of the contact members are connected by suitable means to the electrical circuitry on the circuit board, such as via the above-mentioned axially extending contact bars connected to or forming the gripper contacts of the probe.

While the probe contact members 166a-c can effect electrical connection with the interface contact members 163a-c in any relatively rotated position of the probe, the probe in the illustrated embodiment uses the pin 155 as a locating key for proper registry between the RFID tag and a tag transmitter/receiver device. This enables use of an RFID that may have a small antenna that necessitates positioning of the RFID within two to three millimeters of a transmitter/receiver that communicates with the RFID device to extract information therefrom. The locating key 155 can seat in a locating slot 171 at the top of the interface device 160 to identify a rotational position of the probe for desired angular positioning of the RFID or other identifying device.

As shown in FIGS. 11-15, the key 155 may be formed by a pin radially and asymmetrically protruding from the drive probe housing, and the locating slot may be a corresponding, asymmetric groove formed in a top plate 174 (FIGS. 11, 14 and 15) of the interface device. Pin asymmetry ensures only one rotational orientation for the device since even a 180° rotation will not allow proper seating within the grove as a symmetric protrusion of the pin would. When the gripper lowers the probe into full seated engagement with the interface device, the locating pin will engage in the locating slot to maintain the rotational orientation of the probe. When the probe is once again grabbed by the gripper, the contacts of the probe will be in a known position for proper alignment of the RFID.

Figure 18:
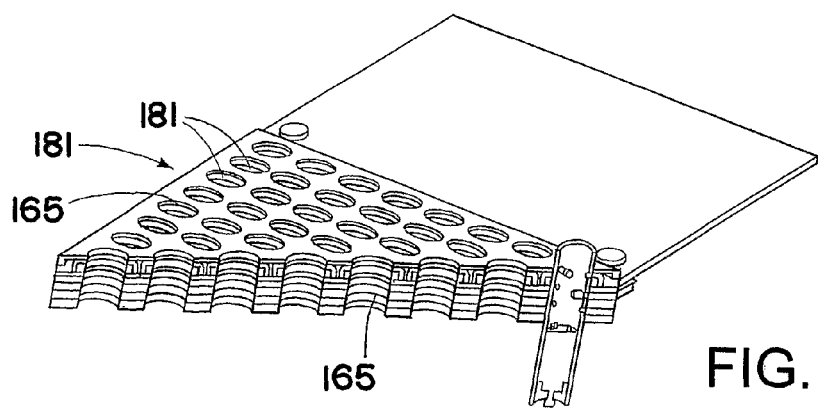
FIG. 18 is a perspective view of an interface grid for interfacing with a plurality of sampling probes.

Referring now to FIG. 18, the insulating and contact plates of the interface device may have a plurality of apertures 180 forming a grid 181 for receiving and interfacing with a plurality of sampling probes. The apertures are arranged in an array with the apertures preferably located at a uniform center-to-center spacing. Communication within these arrays is accomplished in one of two ways. One is where each aperture (and hence each syringe) within the array has a unique communication connection with the controller and each syringe can be and is addressed independently by the controller by routing the signal to the proper array element. The other way is where the communication layer is a simple conductive plate and all communications are broadcast throughout the array. Individual syringes may be addressed by preceding commands with a unique syringe identification contained in the syringe's non-volatile memory. Both approaches may be used. The power and ground layers may consist of simple, conductive plates providing these utilities to all syringes within the array.

Figure 19:
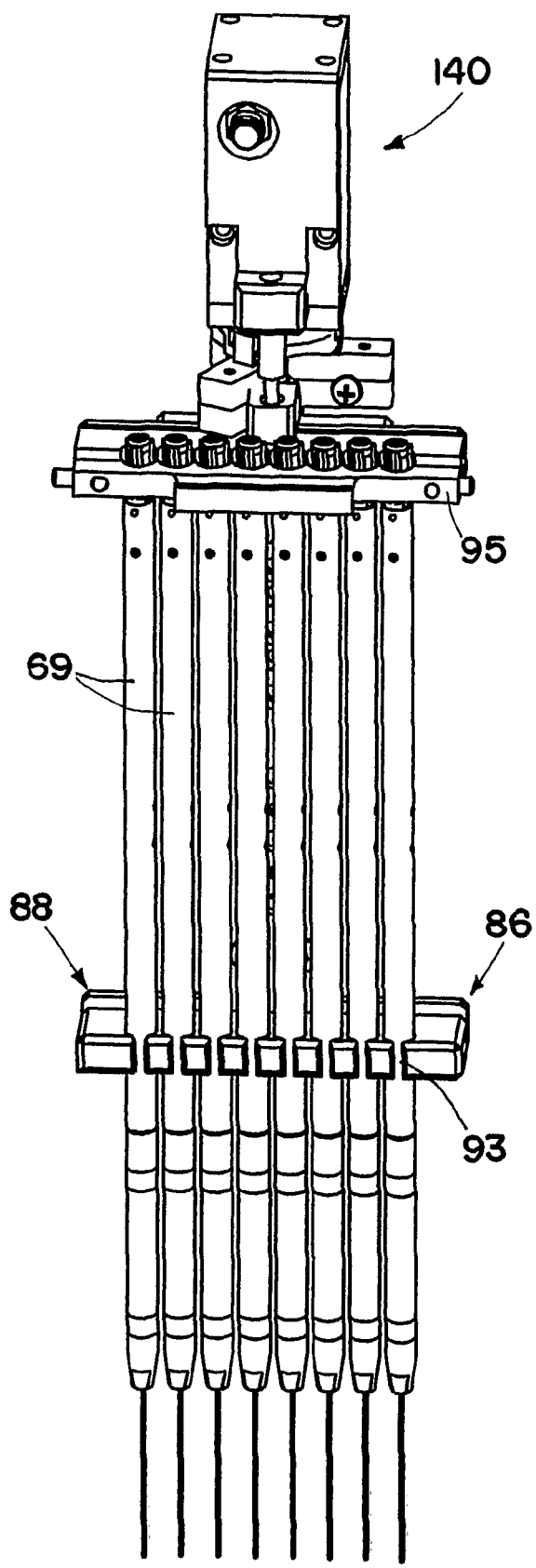
FIG. 19 is a front view of a gang of syringes contained in a carrier with a 9 mm center to center spacing in this example.
Figure 20:
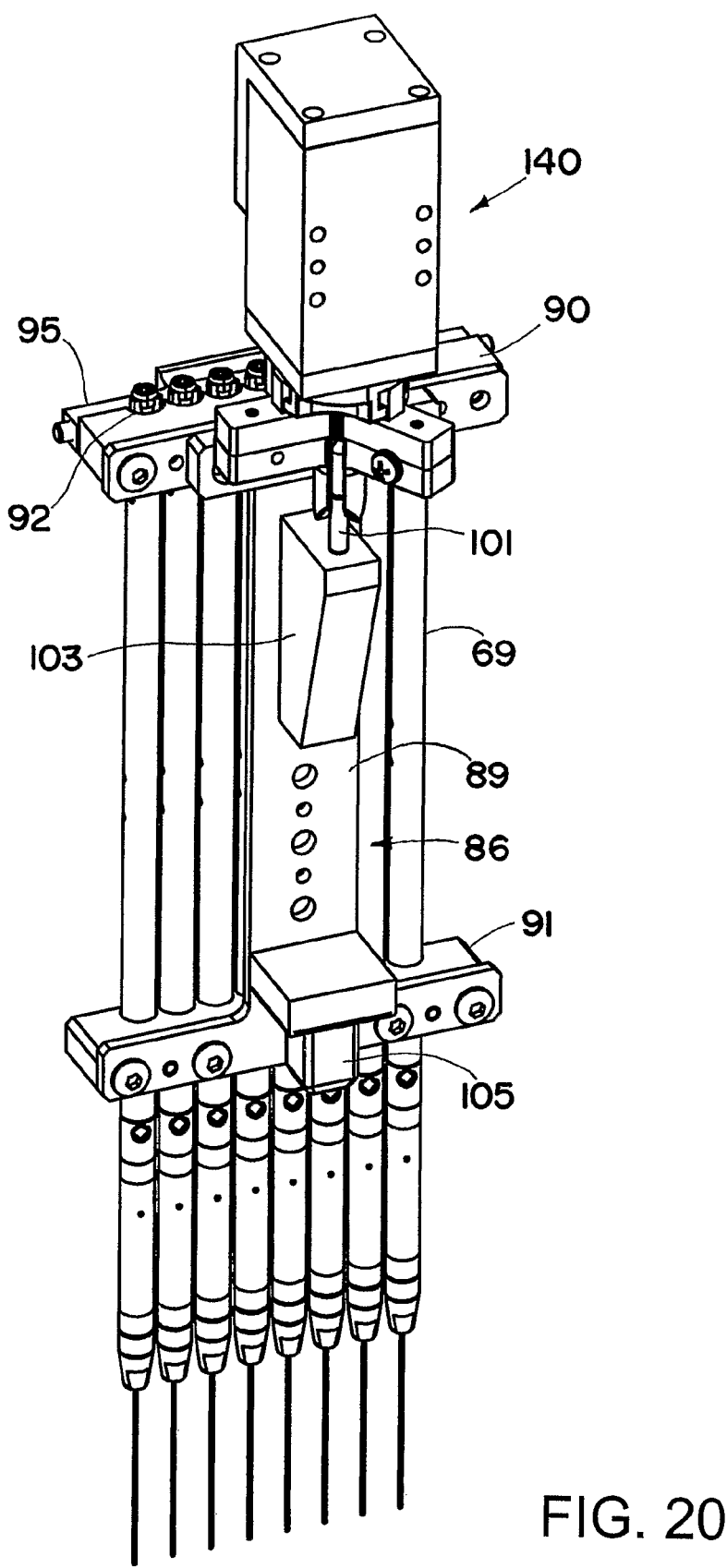
FIG. 20 is a back view of the ganged syringes of FIG. 19.

Referring now to FIGS. 19 and 20, a plurality of sampling probes 69 may be ganged together. In the illustrated embodiment, a gang of eight probes are contained in a carrier (holder) 86 with a 9 mm center to center spacing, although it will be appreciated that the spacing can be more or less and the number of probes can be varied as desired. A 9 mm center to center spacing is particularly desirable since it corresponds to conventional spacing used in 96 position racks/trays. The ganged probes function as an eight channel device for high throughput. That is, eight samples at a time, for example, can be transferred directly from a microwell plate with 9 mm spacing between wells to a 96 position or other device. As indicated, the number of ganged probes can be varied. By way of further example, the carrier could contain 96 probes arranged for example in an 8×12 array to provide 96 channels.

Although carriers of various configurations could be used, the illustrated carrier 86 comprises a frame 88 including a central post 89 that interconnects upper and lower bars or racks 90 and 91. The racks have respective rows of slots 92 and 93 wherein the slots in each row are vertically aligned with respective slots in the other rack. The sampling probes are laterally supported in the slots against any significant lateral movement. In addition, the sampling probes are held against any significant vertical movement by a retention bar 95 attached to the upper rack (or by any other suitable means). The retention bar can be released to allow insertion of the probes into the racks and then closed to grip and thus hold the upper ends of the probes to the upper rack against vertical movement. The upper rack and retention bar have associated therewith contacts for engaging the probe contacts to effect electrical connection and/or communication between the probes and carrier.

The carrier 86 enables the gang of probes to be moved as a unit, such as by a gripper 140. The carrier includes a gripper post 101 having a configuration similar to that of the gripper portion of the connector module of a probe. That is, the post includes grooves in which the fingers of the gripper can engage and the grooves may have associated therewith contacts that are engaged by the contacts of the gripper when the post is gripped by the gripper. The gripper post may be provided on a lug 103 projecting from the backside of the carrier as shown in FIG. 20.

The contacts of the gripper post 101 may be connected to the contacts that engage the contacts of the probes 69 when the latter are secured in the carrier, thereby enabling power, ground and/or communication to be supplied to probes during transport by the gripper. The gripper post contacts may also be connected to respective contacts provided in a plug 105 on the carrier 86 that can plug into a socket of a grid module or other device to enable power, ground and/or communication to be supplied to the probes when the carrier is plugged into a grid module or other device and the gripper is released from the gang to perform other operations.

The carrier 86 may be plugged into (or formed integrally with) a hand-transportable element capable of programming each syringe in the carrier from a local interface or from a PC connection (wired or wireless) whereby each syringe in the collection may be instructed to perform parallel general laboratory operations such as aspirating, dispensing, aliquoting, dilution, reactions, being placed onto a sample injection device for sample introduction into LC or GC equipment, or other general laboratory operations. Sampling probes used in this manner can obviate transfers from container to container in as much as each probe serves as a container through several unit operations. In a practical sense, collections of probes can be handed from lab to lab or group to group for continued use throughout a sample's workflow. This has the benefit of reducing the number of surfaces with which the sample comes in contact and thus reduces sample loss commensurate with adsorption of sample molecule to such surfaces.

Figure 21:
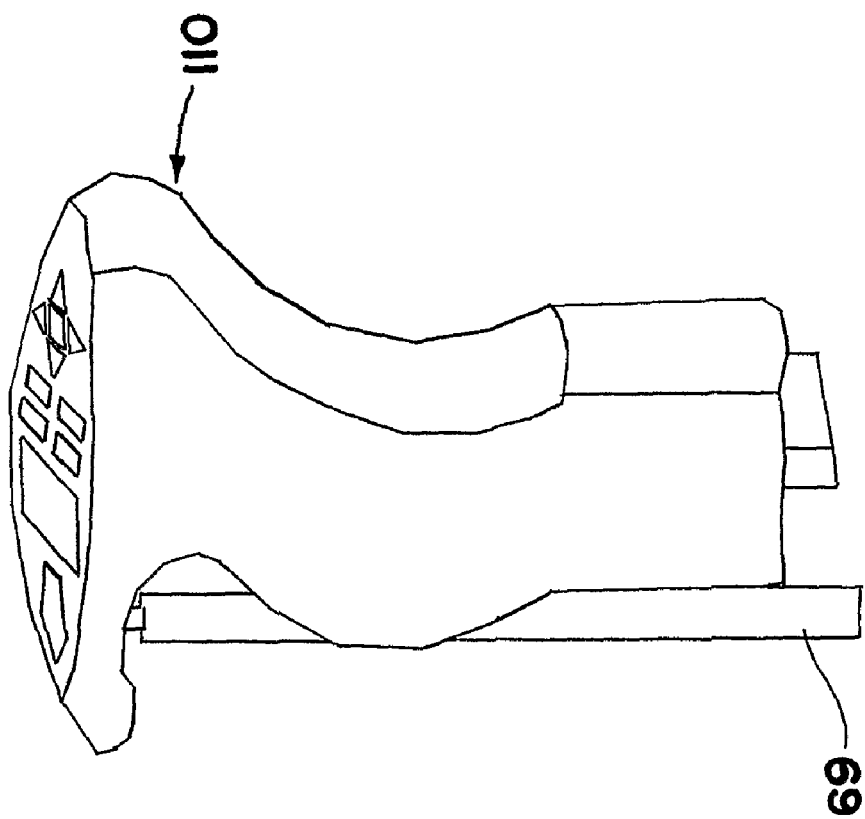
FIG. 21 is an illustration of a hand-held device to which a sampling probe is connected.
Figure 21A:
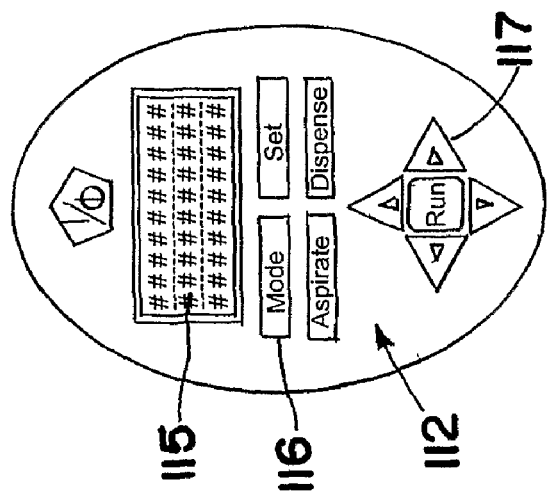
FIG. 21A is a plan view of a user interface employed in the hand-held device of FIG. 21.

In FIG. 21, a hand-held carrier device 110 for a single sampling probe 69 is shown, but it will be appreciated the device can be configured to carry a plurality of sampling probes. The hand-held device may be tethered or untethered. If untethered, the device may carry its own power supply (e.g. battery) and may communicate wirelessly with the overall system controller. The hand-held device in either case may include it own processor and/or interface. An exemplary interface 112 is shown in FIG. 21A. As shown the interface 112 may include a display 115 and various user input devices such as buttons 116 and a navigating device 117. The processor and interface enable the probe and/or device to programmed to perform laboratory operations and or communicate with the technician that is carrying and/or manipulating the hand-held device.

Figure 22:
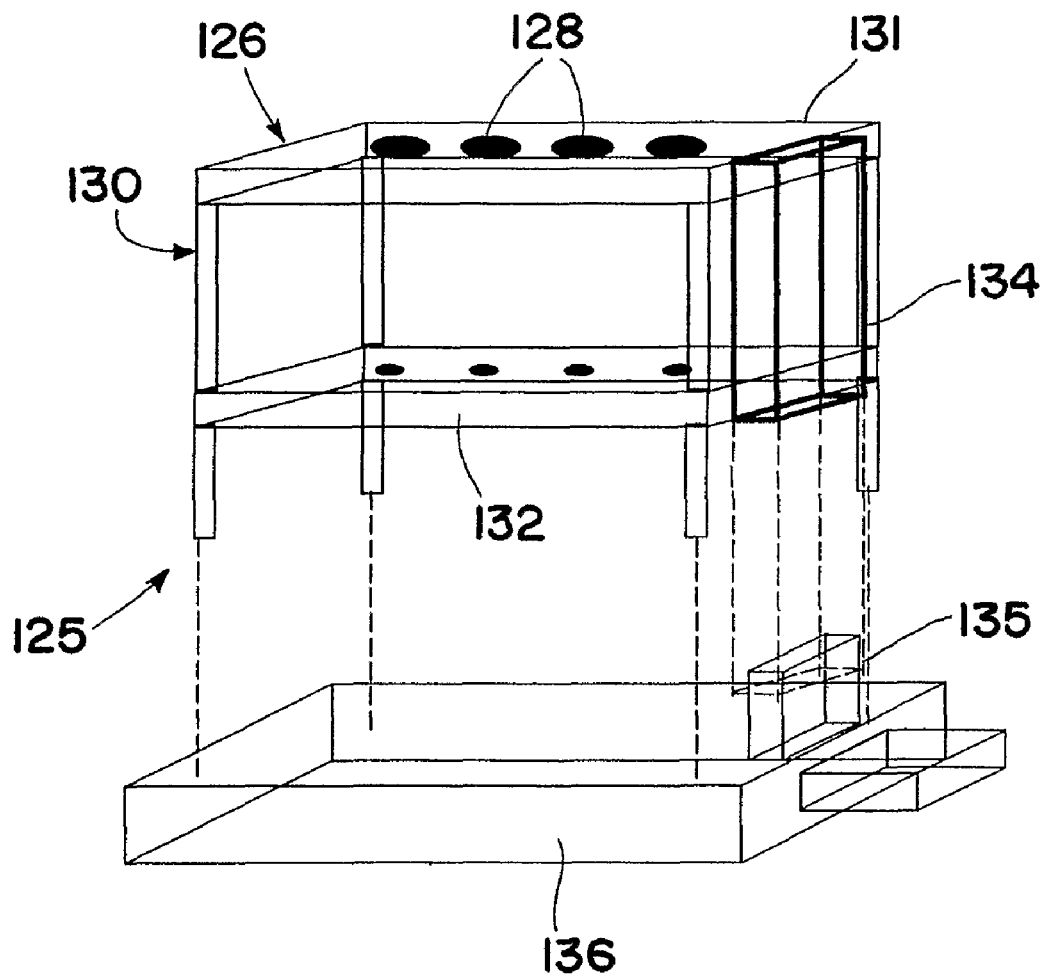
FIG. 22 is schematic illustration of a laboratory park station for the sampling probes.

FIG. 22 is a schematic illustration of a laboratory park station 125. The park station includes a probe holder 126 configured to hold one or more probes. The illustrated holder has four positions 128 into which probes can be inserted. The holder has a frame 130 including upper and lower racks 131 and 132 which may be similar to the upper and lower racks of the carrier shown in FIGS. 19 and 20. Interchangeable standard- and deep-well heights may be provided. Like the carrier of FIGS. 19 and 20, the holder has provision for electrically connecting the probes held therein to a station controller 134 which may be cabled or wireless. The controller may have a connector for connecting to a connector 135 on a base 136 that provides for connection to the overall system controller, which may be a suitably programmed microcomputer and/or computer network.

Figure 23:
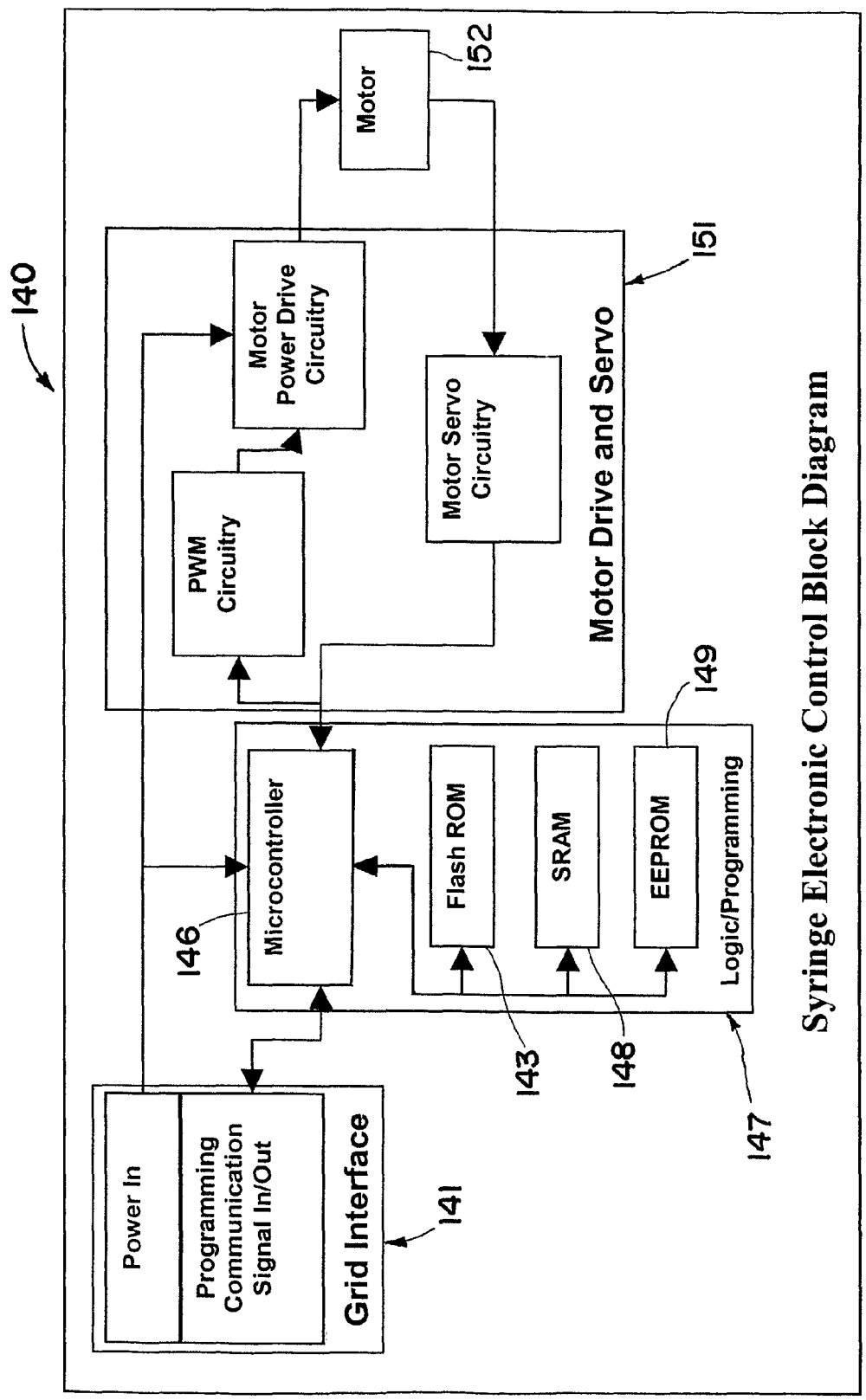
FIG. 23 is a diagrammatic illustration of exemplary electronic control circuitry employed in the sampling probe.

Referring now to FIG. 23, the probe electronics 140 include various components that may all be contained with the probe 69. As above discussed, power may be brought in through a grid interface section 141 (either via a pogo pin connection with grid or via the electrical connection with gripper). Power may be split into clean power for all logic circuitry and dirty/raw power for motor power drive circuitry. The circuitry preferable is designed to be able to write all critical information to flash ROM 143 if power is interrupted (safe power down). Programming instructions may be brought to a microcontroller 146 via the grid's communication signal in and out line. A Logic/Programming section 147 utilizes the flash ROM, SRAM 148, and EEPROM 149 to accept, store, interpret, and execute the programmed instructions downloaded to the probe. The Logic/Programming section utilizes the flash ROM to store execution history information until upload back to the off-syringe control device. A motor drive and servo section 151 takes input from the microcontroller and converts it into motor commutation signals to drive the motor 152. The motor drive and servo section may be provided to take feedback from the motor to verify its operation and position. If desired, provision can be made for sensing a motor stall and communicating a sensed stall to the main system.

In particular, the probe (syringe) controller 140 may be a printed circuit assembly contained within the autonomous probe. The assembly may be a microcontroller-based motor controller which is responsible for multiple tasks including receiving commands and workflow from the deck controller, log workflow/method primitives in local non-volatile memory, and/or control a brushless DC motor commutation and speed. The probe controller circuit assembly receives signals from the grid.

The probe controller electronics hardware may be partitioned into three functional sections: power regulation, microcontroller and/or motor driver. The power supplied to the probe may be split into power for the brushless DC motor and power for the microcontroller and peripheral circuitry, with the intent to separate clean power from dirty power. Preferably capacitance is added to the clean power signal allowing it to stay up for a period of time after the input power is removed. This time period can be used to write state information to an EEPROM or equivalent.

The microcontroller, such as an Atmel ATmega168V microcontroller) may be responsible for multiple tasks within the Probe controller, such as grid communications control, motor control and/or EEPROM control. The microcontroller may use an internal UART to communicate via the grid with a deck controller (system controller). Communications may be half-duplex on a single wire.

The brushless DC motor may be controlled using a 3 phase bridge. The microcontroller may be responsible for commutating the motors under program control. Hall sensors incorporated with the motor may provide orientation feedback required for motor commutation. Motor speed may be controlled by limiting the available current per phase of motor commutation. Speed may be sensed by measuring the period between successive Hall interrupts. In turn, motor current may be controlled by pulse-width-modulating (PWM) the low side driving (sinking) FETs in the 3 phase bridge. The PWM signal may be generated using hardware integral to the microcontroller.

Motor current may be monitored using a sense resistor and differential amplifier on the low side of the 3 phase bridge. Two poles of low pass filtering may be provided to attenuate the PWM modulation. In addition, a comparator may sense an over-current condition and interrupt the microcontroller; thereby allowing for a timely shut down in the event of excessive current.

An EEPROM (for example an Atmel AT24C512) may be used for the audit trail and for saving state information (plunger location, time, etc.) in the event of inadvertent power failure.

A probe management scheme may have the following functionality: syringe configuration storage/retrieval, calculation of run-time parameters using configuration information, track plunger cycles, sleep and wake-up control, power down detection and state information storage, error handling and posting, non-volatile data storage management, and communication management. The communication management may provide the following functionality: demand request slave operation, multiplexed Tx/Rx asynchronous serial-to-single wire bus, multi-processor mode command address filtering, inter-character gap timeout monitoring, wake-up on character, command/response data integrity and command filtering. The workflow management may provide the following functionality: workflow storage/retrieval, workflow sequencing, workflow interpretation, workflow execution, workflow audit logging, and workflow cataloging. The motion control may provide the following functionality: motor speed control, motor current control, acceleration/deceleration profile, brushless dc motor drive (state transitions, rotational speed, position and direction), plunger position and movement, and plunger position calibration.

The host controller commands may serve to control syringe operations directly and/or configure workflows/method primitives for future execution. In addition, these commands may illicit responses that provide syringe status and configuration information. Workflows/method primitives may be stored and removed under host controller supervision throughout the syringe's product life. This data may be accessed by both the syringe and the host controller during normal operation. Audit logs may be stored by the syringe during command and workflow/method primitive execution.

The audit logs may be read and removed under host controller supervision. This data may be accessed by both the syringe and the host controller during normal operation. An operational snap-shot is stored in response to loss of power. This data may be accessed by the syringe at power-down and power-up.

A multi-character binary command set may be used between the host controller and syringe. Each syringe may be assigned an 8-bit "logical address" by the host controller when introduced to the system. This logical address may be maintained in a non-volatile fashion. In addition, a "broadcast" logical address may be allocated that all syringes will accept, but not generate a response. The logical address may be the first character in every message followed by the command, optional data length, optional data characters and a checksum. The command may be processed and every command may result in a response with the exception of commands sent to the "broadcast" logical address.

The method primitives that comprise a workflow may consist of a unique 1-byte opcode, a 1-byte length value and optional data. As the method primitive is retrieved from non-volatile memory it may be interpreted to configure the associate syringe operation. The opcode may define both the operation and the type/units for any associated data. In some cases the data may be provided in volume and volume/second units which must be converted to motion control values.

Figure 24:
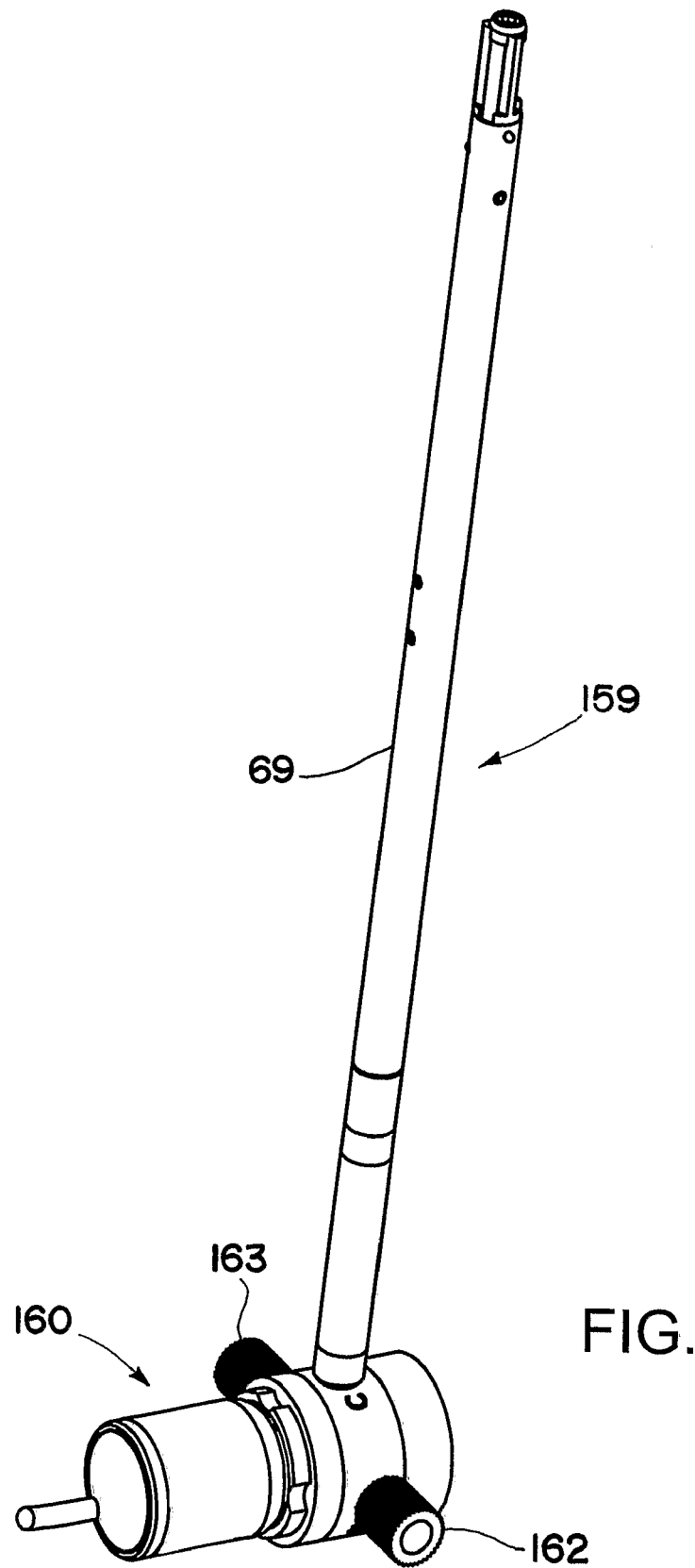
FIG. 24 is a perspective view of the sampling probe configured to function as a syringe pump.

Turning now to FIG. 24, the probe 69 can be converted into a syringe pump 159 by replacing the needle with a three-way or similarly functioning valve mechanism 160. The valve mechanism 160 provides the ability to fluidically connect the lumen of the barrel to a liquid source in one setting and an output device, container, or surface in another setting to coordinate pumping fluid from the liquid source to the output device, container, or surface as the syringe retracts and extends its plunger. To this end, the valve mechanism has input and output ports 162 and 163 for connecting to the liquid source and output device, container, etc.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A sampling probe comprising a drive module having a reciprocating drive coupling, and a syringe module removably coupled coaxially to the drive module to allow for different syringe modules to be interchangeably coupled to the drive module, wherein the syringe module includes a plunger barrel, a plunger movable in the plunger barrel, and a plunger rod extending from an end of the plunger barrel for removable coupling to the drive coupling of the drive module for effecting common reciprocating movement of the plunger rod with the drive coupling, and the drive module and syringe module have cylindrical outer surfaces of the same outer diameter such that together the modules provide the probe with a substantially continuous cylindrical outer surface of uniform diameter;

wherein the drive module and syringe module include a drive module housing and a syringe module housing, respectively; and wherein the drive module housing houses a drive motor and a rotary-to-linear motion transfer device interposed between the drive motor and drive coupling.

2. A sampling probe according to claim 1, wherein the drive module and syringe module are removably coupled by mating threads permitting the syringe module to be screwed onto and off of the drive module.

3. A sampling probe according to claim 1, wherein the syringe module housing includes a transparent or translucent plunger barrel.

4. A sampling probe according to claim 1, wherein the syringe module housing includes a plunger barrel, and the syringe module includes an end piece attached to an end of the plunger barrel and threaded for connection to a mating threaded portion of the drive module housing.

5. A sampling probe according to claim 1, wherein the drive module includes electrical circuitry including motor control circuitry, and a connector assembly for connecting the electrical circuitry to an external device external to the sampling probe.

6. A sampling probe according to claim 1, wherein the syringe module housing forms a continuation of the drive module housing when coupled thereto.

7. A sampling probe according to claim 6, wherein the syringe module housing and the drive module housing have mating threaded portions for removably coupling one to the other.

8. A sampling probe according to claim 1, wherein the drive coupling is an axially movable drive member, and the drive member and plunger rod include mating coupling members providing for quick connection and disconnection of the plunger and drive member.

9. A sampling probe according to claim 8, wherein the mating coupling members include a ball and a socket for the ball.

10. A sampling probe comprising a drive module and a syringe module removably coupled coaxially to the drive module to allow for different syringe modules to be interchangeably coupled to the drive module, wherein the drive module and syringe module include a drive module housing and a syringe module housing, respectively; wherein the drive module housing houses a drive motor and a rotary-to-linear motion transfer device, and the syringe module housing contains a plunger configured at one end for detachable coupling to the rotary-to-linear motion transfer device; and wherein at least one of the transfer device and plunger includes a stem terminating at an enlarged head, and the other includes a coupling body having a side slot with a narrow portion extending from an end of the coupling body to a wider portion of the side slot, the narrow portion being sized to receive the stem but less than the width of the enlarged head, and the wider portion being sized to receive the enlarged head, whereby the plunger can be quickly and easily engaged and disengaged with respect to the transfer device.

* * * * *

UNITED STATES PATENT AND TRADEMARK OFFICE
CERTIFICATE OF CORRECTION

PATENT NO. : 8,057,756 B2  
APPLICATION NO. : 11/814987  
DATED : November 15, 2011  
INVENTOR(S) : Thomas R. Londo et al.

Page 1 of 1

It is certified that error appears in the above-identified patent and that said Letters Patent is hereby corrected as shown below:

On the Title Page, Item (60):
"Related U.S. Application Data
Provisional application No. 60/648,213, filed on Jan. 28, 2005." should read:
-- Related U.S. Application Data
Provisional application No. 60/648,213, filed on Jan. 28, 2005 and provisional application No. 60/761,151, filed on Jan. 23, 2006. --

In the Specification

Column 1, lines 13-16:
"U.S. Provisional Application No. of the same title as above and filed Jan. 23, 2006, both of which are hereby incorporated herein by reference in their entireties." should read:
-- U.S. Provisional Application No. 60/761,151 filed Jan. 23, 2006, both of which are hereby incorporated herein by reference in their entireties. --

Signed and Sealed this
Twenty-ninth Day of October, 2013

Teresa Stanek Rea
*Deputy Director of the United States Patent and Trademark Office*